(12) United States Patent
Dancs et al.

(10) Patent No.: US 7,589,340 B2
(45) Date of Patent: Sep. 15, 2009

(54) SYSTEM FOR DETECTING A CONTAINER OR CONTENTS OF THE CONTAINER

(75) Inventors: Imre J. Dancs, Greenfield, WI (US); Jeffrey L. Harwig, New Berlin, WI (US); John A. Heathcock, Racine, WI (US); Dennis W. Gruber, Arlington Heights, IL (US); Eric B. Gach, Mount Prospect, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 666 days.

(21) Appl. No.: 11/096,920

(22) Filed: Mar. 31, 2005

(65) Prior Publication Data

US 2006/0219962 A1    Oct. 5, 2006

(51) Int. Cl.
*G01N 15/06* (2006.01)
*G01F 23/00* (2006.01)
(52) U.S. Cl. ............... 250/577; 73/290 R; 356/436
(58) Field of Classification Search ................ 250/576, 250/577; 73/290 R; 356/246, 436, 440, 356/442
See application file for complete search history.

(56) References Cited

U.S. PATENT DOCUMENTS

| | | |
|---|---|---|
| 38,150 A | 4/1863 | Colburn |
| 446,953 A | 2/1891 | Robert |
| 514,422 A | 2/1894 | Kellogg |
| 554,115 A | 2/1896 | Fisher |
| 699,652 A | 5/1902 | Campbell et al. |
| 1,178,575 A | 4/1916 | Collins |
| 1,403,548 A | 1/1922 | Gudeman |
| 1,712,204 A | 5/1929 | Gibney |
| 1,751,257 A | 3/1930 | Vallebuona et al. |
| 1,800,156 A | 4/1931 | Rotheim |
| 1,977,997 A | 10/1934 | Patterson et al. |
| 1,981,650 A | 11/1934 | Larsen |
| 1,994,932 A | 3/1935 | Vidal |
| 2,192,019 A | 2/1940 | Schepmoes |
| 2,230,265 A | 2/1941 | Robinson |
| 2,372,371 A | 3/1945 | Eisner |
| 2,424,268 A | 7/1947 | Delane et al. |
| 2,435,756 A | 2/1948 | Schlesinger |
| 2,469,656 A | 5/1949 | Lienert |

(Continued)

FOREIGN PATENT DOCUMENTS

DE    3609511    10/1986

(Continued)

OTHER PUBLICATIONS

Search Report in International Application No. PCT/US2006/011872 along with Written Opinion, both dated Aug. 2, 2006 (17 pages).

(Continued)

*Primary Examiner*—Thanh X Luu

(57) ABSTRACT

A system for detecting a container or contents of the container. The system includes a diffuser for retaining the container, where the container is configured to hold an active material therein and may include a wick extending therefrom. The system further includes a sensor positioned to detect, for example, the container retained in the diffuser and/or the contents of the container retained in the diffuser.

12 Claims, 13 Drawing Sheets

U.S. PATENT DOCUMENTS

| | | | |
|---|---|---|---|
| 2,557,501 | A | 6/1951 | Fusay et al. |
| 2,591,818 | A | 4/1952 | Huff |
| 2,597,195 | A | 5/1952 | Smith |
| 2,668,993 | A | 2/1954 | Bair |
| 2,931,880 | A | 4/1960 | Yaffe |
| 2,942,090 | A | 6/1960 | Diehl |
| 3,248,530 | A | 4/1966 | Titmas |
| 3,358,552 | A | 12/1967 | Schneider |
| 3,373,341 | A | 3/1968 | Wattson |
| 3,386,005 | A | 5/1968 | Roland et al. |
| 3,436,310 | A | 4/1969 | Arnold et al. |
| 3,443,083 | A | 5/1969 | Curran |
| 3,543,122 | A | 11/1970 | Klebanoff et al. |
| 3,545,650 | A | 12/1970 | Williams |
| 3,588,859 | A | 6/1971 | Petree |
| 3,615,041 | A | 10/1971 | Bischoff |
| 3,747,902 | A | 7/1973 | Rushton |
| 3,780,260 | A | 12/1973 | Elsner |
| 3,790,772 | A | 2/1974 | Newman et al. |
| 3,864,080 | A | 2/1975 | Valbona et al. |
| 3,872,280 | A | 3/1975 | Van Dalen |
| 3,948,445 | A | 4/1976 | Andeweg |
| 4,084,079 | A | 4/1978 | Costello |
| 4,106,671 | A | 8/1978 | Sharples |
| 4,166,293 | A | 9/1979 | Anis |
| 4,184,612 | A | 1/1980 | Freyre |
| 4,197,671 | A | 4/1980 | De Brouwer |
| 4,202,387 | A | 5/1980 | Upton |
| 4,217,315 | A | 8/1980 | Keeler, II |
| 4,223,231 | A * | 9/1980 | Sugiyama ................ 250/577 |
| 4,229,415 | A | 10/1980 | Bryson |
| 4,244,525 | A | 1/1981 | Manna |
| 4,250,537 | A | 2/1981 | Roegner et al. |
| 4,285,028 | A | 8/1981 | Sundin et al. |
| 4,301,095 | A | 11/1981 | Mettler et al. |
| 4,315,665 | A | 2/1982 | Haines |
| 4,338,547 | A | 7/1982 | McCaslin |
| 4,346,059 | A | 8/1982 | Spector |
| 4,391,781 | A | 7/1983 | van Lit |
| 4,415,797 | A | 11/1983 | Choustoulakis |
| 4,432,938 | A | 2/1984 | Meetze, Jr. |
| 4,435,732 | A | 3/1984 | Hyatt |
| 4,493,011 | A | 1/1985 | Spector |
| 4,549,250 | A | 10/1985 | Spector |
| 4,571,485 | A | 2/1986 | Spector |
| 4,583,686 | A | 4/1986 | Martens et al. |
| 4,597,781 | A | 7/1986 | Spector |
| 4,609,978 | A | 9/1986 | Hsieh et al. |
| 4,611,266 | A | 9/1986 | Schwartz |
| 4,666,638 | A | 5/1987 | Baker et al. |
| 4,670,820 | A | 6/1987 | Eddins et al. |
| 4,689,515 | A | 8/1987 | Benndorf et al. |
| 4,702,418 | A | 10/1987 | Carter et al. |
| 4,703,155 | A | 10/1987 | Suhajda |
| 4,703,314 | A | 10/1987 | Spani |
| 4,707,338 | A | 11/1987 | Spector |
| 4,714,984 | A | 12/1987 | Spector |
| 4,715,702 | A | 12/1987 | Dillon |
| 4,739,928 | A | 4/1988 | O'Neil |
| 4,750,471 | A | 6/1988 | Hautmann et al. |
| 4,795,883 | A | 1/1989 | Glucksman et al. |
| 4,816,973 | A | 3/1989 | Atalla et al. |
| 4,830,791 | A | 5/1989 | Muderlak et al. |
| 4,837,421 | A | 6/1989 | Luthy |
| 4,840,444 | A | 6/1989 | Hewitt |
| 4,844,050 | A | 7/1989 | Hautmann et al. |
| 4,849,606 | A | 7/1989 | Martens, III et al. |
| 4,856,103 | A | 8/1989 | Compton |
| 4,858,079 | A | 8/1989 | Ohashi |
| 4,866,580 | A | 9/1989 | Blackerby |
| 4,870,551 | A | 9/1989 | Nagel |
| 4,873,029 | A | 10/1989 | Blum |
| 4,934,792 | A | 6/1990 | Tovi |
| 4,955,714 | A | 9/1990 | Stotler et al. |
| 4,968,487 | A | 11/1990 | Yamamoto et al. |
| 5,017,909 | A | 5/1991 | Goekler |
| 5,038,394 | A | 8/1991 | Hasegawa et al. |
| 5,055,822 | A | 10/1991 | Campbell et al. |
| 5,095,647 | A | 3/1992 | Zobele et al. |
| 5,111,477 | A | 5/1992 | Muderlak |
| 5,115,975 | A | 5/1992 | Shilling |
| 5,118,319 | A | 6/1992 | Smith et al. |
| 5,135,485 | A | 8/1992 | Cohen et al. |
| 5,136,483 | A | 8/1992 | Schoniger et al. |
| 5,147,585 | A | 9/1992 | Blum |
| 5,175,791 | A | 12/1992 | Muderlak et al. |
| 5,201,025 | A | 4/1993 | Landesberg |
| 5,213,523 | A | 5/1993 | Hygema et al. |
| 5,214,458 | A | 5/1993 | Kanai |
| 5,222,186 | A | 6/1993 | Schimanski et al. |
| 5,230,837 | A | 7/1993 | Babasade |
| 5,233,375 | A | 8/1993 | Williams et al. |
| 5,260,919 | A | 11/1993 | Tsai |
| 5,274,215 | A | 12/1993 | Jackson |
| 5,283,601 | A | 2/1994 | Lowe |
| 5,283,723 | A | 2/1994 | Wu |
| 5,309,185 | A | 5/1994 | Harper |
| 5,309,338 | A | 5/1994 | Liu |
| 5,324,490 | A | 6/1994 | Van Vlahakis |
| D350,209 | S | 8/1994 | Martin |
| 5,370,829 | A | 12/1994 | Kunze |
| 5,382,410 | A | 1/1995 | Peltier |
| D357,330 | S | 4/1995 | Wong et al. |
| 5,419,879 | A | 5/1995 | Vlahakis et al. |
| 5,432,623 | A | 7/1995 | Egan et al. |
| 5,449,117 | A | 9/1995 | Muderlak et al. |
| 5,452,270 | A | 9/1995 | Ikeda et al. |
| 5,464,710 | A | 11/1995 | Yang |
| 5,483,689 | A | 1/1996 | O'Donnell, Jr. et al. |
| 5,484,086 | A | 1/1996 | Pu |
| 5,485,308 | A | 1/1996 | Hirata et al. |
| 5,497,102 | A | 3/1996 | Burrows et al. |
| 5,498,397 | A | 3/1996 | Horng |
| 5,512,371 | A | 4/1996 | Gupta et al. |
| 5,517,264 | A | 5/1996 | Sutton |
| 5,521,357 | A | 5/1996 | Lock et al. |
| 5,524,101 | A | 6/1996 | Thorgersen et al. |
| D372,769 | S | 8/1996 | Ganor |
| 5,544,812 | A | 8/1996 | Torres |
| 5,549,247 | A | 8/1996 | Rossman et al. |
| 5,556,192 | A | 9/1996 | Wang |
| 5,591,409 | A | 1/1997 | Watkins |
| 5,616,172 | A | 4/1997 | Tuckerman et al. |
| 5,633,623 | A | 5/1997 | Campman |
| D381,443 | S | 7/1997 | Yuen |
| D381,444 | S | 7/1997 | Yuen |
| 5,647,053 | A | 7/1997 | Schroeder et al. |
| 5,662,835 | A | 9/1997 | Collingwood |
| 5,690,509 | A | 11/1997 | Eisenbraun |
| D386,974 | S | 12/1997 | Wefler |
| 5,716,119 | A | 2/1998 | Patel |
| D393,063 | S | 3/1998 | Wefler |
| 5,752,766 | A | 5/1998 | Bailey et al. |
| 5,757,111 | A | 5/1998 | Sato |
| 5,757,459 | A | 5/1998 | Bhalakia et al. |
| D395,529 | S | 6/1998 | Yuen |
| 5,763,080 | A | 6/1998 | Stahl et al. |
| 5,772,074 | A | 6/1998 | Dial et al. |
| 5,788,931 | A | 8/1998 | Quintana |
| 5,830,578 | A | 11/1998 | Ono et al. |
| 5,852,946 | A | 12/1998 | Cowger |
| 5,863,108 | A | 1/1999 | Lederer |
| 5,871,153 | A | 2/1999 | Doggett, Jr. |
| 5,875,968 | A | 3/1999 | Miller et al. |

| | | | | | | |
|---|---|---|---|---|---|---|
| 5,876,678 | A | 3/1999 | Harrell et al. | 6,392,549 | B1 | 5/2002 | Wu |
| 5,903,710 | A | 5/1999 | Wefler et al. | D458,395 | S | 6/2002 | Piepgras |
| 5,909,845 | A | 6/1999 | Greatbatch et al. | 6,398,381 | B1 | 6/2002 | Tseng |
| 5,922,231 | A | 7/1999 | Karst et al. | 6,409,302 | B2 * | 6/2002 | Altfather et al. .............. 347/19 |
| 5,924,784 | A | 7/1999 | Chliwnyj et al. | D460,544 | S | 7/2002 | Garcia |
| D412,569 | S | 8/1999 | Muller | D460,573 | S | 7/2002 | Gee, II |
| 5,937,140 | A | 8/1999 | Leonard et al. | 6,420,877 | B1 | 7/2002 | Replogle |
| 5,940,577 | A | 8/1999 | Steinel | 6,423,892 | B1 | 7/2002 | Ramaswamy |
| 5,945,094 | A | 8/1999 | Martin et al. | D461,549 | S | 8/2002 | Garcia |
| 5,964,519 | A | 10/1999 | Chun-Ying | D461,885 | S | 8/2002 | Jordi |
| 5,976,503 | A | 11/1999 | Martin et al. | 6,431,719 | B1 | 8/2002 | Lau et al. |
| 5,980,064 | A | 11/1999 | Metroyanis | 6,439,471 | B2 | 8/2002 | Ehrlich et al. |
| 6,016,038 | A | 1/2000 | Mueller et al. | D462,755 | S | 9/2002 | Millan |
| 6,020,983 | A | 2/2000 | Neu et al. | D463,610 | S | 9/2002 | Piepgras |
| 6,039,899 | A | 3/2000 | Martin et al. | 6,446,880 | B1 | 9/2002 | Schram et al. |
| 6,044,202 | A | 3/2000 | Junkel | D464,416 | S | 10/2002 | von Dohlen et al. |
| 6,072,606 | A | 6/2000 | Huether et al. | 6,457,826 | B1 | 10/2002 | Lett |
| 6,097,881 | A | 8/2000 | DeWitt et al. | 6,459,919 | B1 | 10/2002 | Lys et al. |
| 6,101,038 | A | 8/2000 | Hebert et al. | 6,466,739 | B2 | 10/2002 | Ambrosi et al. |
| 6,104,866 | A | 8/2000 | DeWitt et al. | 6,471,193 | B2 | 10/2002 | Warren |
| 6,104,867 | A | 8/2000 | Stathakis et al. | 6,478,440 | B1 | 11/2002 | Jaworski et al. |
| 6,123,935 | A | 9/2000 | Wefler et al. | 6,479,594 | B1 | 11/2002 | Cheung et al. |
| 6,135,369 | A | 10/2000 | Prendergast et al. | 6,482,863 | B2 | 11/2002 | Munagavalasa et al. |
| D433,521 | S | 11/2000 | Jaworski | D468,033 | S | 12/2002 | Warren et al. |
| D433,744 | S | 11/2000 | Basaganas | D468,035 | S | 12/2002 | Blanc et al. |
| 6,142,653 | A | 11/2000 | Larson | 6,503,459 | B1 | 1/2003 | Leonard et al. |
| 6,145,241 | A | 11/2000 | Okuno | D469,862 | S | 2/2003 | Cruver, IV et al. |
| 6,149,283 | A | 11/2000 | Conway et al. | 6,528,954 | B1 | 3/2003 | Lys et al. |
| 6,150,774 | A | 11/2000 | Mueller et al. | 6,536,746 | B2 | 3/2003 | Watkins |
| 6,150,943 | A | 11/2000 | Lehman et al. | D473,638 | S | 4/2003 | Cruver, IV |
| 6,151,827 | A | 11/2000 | Smith et al. | 6,547,553 | B2 | 4/2003 | Koch et al. |
| 6,153,703 | A | 11/2000 | Lustiger et al. | 6,548,967 | B1 | 4/2003 | Dowling et al. |
| 6,154,607 | A | 11/2000 | Flashinski et al. | 6,554,203 | B2 | 4/2003 | Hess et al. |
| D434,842 | S | 12/2000 | Thomas et al. | 6,557,998 | B2 | 5/2003 | Portney |
| 6,163,098 | A | 12/2000 | Taylor et al. | 6,558,022 | B2 | 5/2003 | Kawahara |
| 6,166,496 | A | 12/2000 | Lys et al. | 6,567,613 | B2 | 5/2003 | Rymer |
| D436,657 | S | 1/2001 | Heatter | 6,569,387 | B1 | 5/2003 | Furner et al. |
| D437,069 | S | 1/2001 | Allison | D475,446 | S | 6/2003 | Millan |
| D437,636 | S | 2/2001 | Basaganas | 6,575,610 | B2 | 6/2003 | Natsume |
| 6,191,826 | B1 | 2/2001 | Murakami et al. | 6,577,080 | B2 | 6/2003 | Lys et al. |
| 6,196,471 | B1 | 3/2001 | Ruthenberg | 6,581,915 | B2 | 6/2003 | Bartsch et al. |
| 6,199,983 | B1 | 3/2001 | Kato et al. | 6,584,986 | B2 | 7/2003 | Gindl |
| 6,211,626 | B1 | 4/2001 | Lys et al. | 6,588,435 | B1 | 7/2003 | Gindl |
| 6,216,925 | B1 | 4/2001 | Garon | 6,602,475 | B1 | 8/2003 | Chiao |
| 6,236,807 | B1 | 5/2001 | Ruffolo et al. | 6,603,924 | B2 * | 8/2003 | Brown et al. ................ 392/390 |
| 6,239,216 | B1 | 5/2001 | Montanari et al. | 6,606,548 | B2 | 8/2003 | Kato et al. |
| 6,241,362 | B1 | 6/2001 | Morrison | 6,608,453 | B2 | 8/2003 | Morgan et al. |
| 6,254,065 | B1 | 7/2001 | Ehrensperger et al. | 6,611,297 | B1 | 8/2003 | Akashi et al. |
| 6,264,548 | B1 * | 7/2001 | Payne et al. ................ 454/157 | 6,619,559 | B2 | 9/2003 | Wohrle et al. |
| 6,267,297 | B1 | 7/2001 | Contadini et al. | 6,622,662 | B1 | 9/2003 | Wolpert et al. |
| 6,268,062 | B1 | 7/2001 | Demeuse | 6,624,597 | B2 | 9/2003 | Dowling et al. |
| 6,270,720 | B1 | 8/2001 | Mandish | D480,792 | S | 10/2003 | Millan |
| 6,275,651 | B1 | 8/2001 | Voit | 6,631,888 | B1 | 10/2003 | Prueter |
| 6,278,840 | B1 | 8/2001 | Basaganas Millan | D481,787 | S | 11/2003 | Millan |
| 6,281,867 | B2 | 8/2001 | Kurematsu | 6,644,507 | B2 | 11/2003 | Borut et al. |
| 6,292,305 | B1 | 8/2001 | Sakuma et al. | D483,104 | S | 12/2003 | Hill et al. |
| 6,292,196 | B1 | 9/2001 | Fukunaga et al. | 6,661,967 | B2 | 12/2003 | Levine et al. |
| 6,292,901 | B1 | 9/2001 | Lys et al. | 6,667,576 | B1 | 12/2003 | Westhoff |
| 6,302,559 | B1 | 10/2001 | Warren | 6,676,284 | B1 | 1/2004 | Wynne Willson |
| 6,337,080 | B1 | 1/2002 | Fryan et al. | 6,681,585 | B1 | 1/2004 | Stagg et al. |
| 6,340,868 | B1 | 1/2002 | Lys et al. | 6,682,331 | B1 | 1/2004 | Peh et al. |
| 6,341,732 | B1 | 1/2002 | Martin et al. | 6,685,339 | B2 | 2/2004 | Daughtry et al. |
| D453,562 | S | 2/2002 | Makino | 6,685,343 | B2 | 2/2004 | Mabuchi |
| 6,350,417 | B1 | 2/2002 | Lau et al. | 6,688,752 | B2 | 2/2004 | Moore |
| 6,361,136 | B1 * | 3/2002 | Watanabe et al. .............. 347/7 | 6,690,120 | B2 | 2/2004 | Oskorep et al. |
| 6,361,752 | B1 | 3/2002 | Demarest et al. | 6,697,571 | B2 | 2/2004 | Triplett et al. |
| D455,486 | S | 4/2002 | Makino | 6,698,665 | B2 | 3/2004 | Minamite et al. |
| 6,368,564 | B1 | 4/2002 | Smith | 6,713,024 | B1 | 3/2004 | Arnell et al. |
| 6,377,164 | B1 | 4/2002 | Fulmer | 6,714,725 | B2 | 3/2004 | Grone et al. |
| D457,667 | S | 5/2002 | Piepgras | 6,717,376 | B2 | 4/2004 | Lys et al. |
| D457,669 | S | 5/2002 | Piepgras | 6,719,217 | B1 | 4/2004 | Tawara et al. |
| D457,974 | S | 5/2002 | Piepgras | 6,720,745 | B2 | 4/2004 | Lys et al. |
| 6,390,453 | B1 | 5/2002 | Frederickson et al. | 6,721,102 | B2 | 4/2004 | Bourdelais et al. |

| Patent Number | Date | Inventor |
|---|---|---|
| 6,727,332 B2 | 4/2004 | Demain |
| 6,729,552 B1 | 5/2004 | McEwen |
| 6,729,746 B2 | 5/2004 | Suehiro et al. |
| 6,733,719 B2 | 5/2004 | DiNardo et al. |
| 6,733,898 B2 | 5/2004 | Kim et al. |
| D491,678 S | 6/2004 | Piepgras |
| D492,042 S | 6/2004 | Piepgras |
| 6,752,327 B2 | 6/2004 | Martens, III et al. |
| 6,758,566 B2 | 7/2004 | Goulden et al. |
| 6,759,961 B2 | 7/2004 | Fitzgerald et al. |
| 6,763,624 B2 | 7/2004 | Gow |
| 6,766,773 B2 | 7/2004 | Wolpert et al. |
| 6,768,865 B2 | 7/2004 | Stathakis et al. |
| 6,774,584 B2 | 8/2004 | Lys et al. |
| 6,775,470 B2 | 8/2004 | Zobele et al. |
| 6,777,891 B2 | 8/2004 | Lys et al. |
| 6,779,905 B1 | 8/2004 | Mazursky et al. |
| 6,781,329 B2 | 8/2004 | Mueller et al. |
| 6,782,194 B2 | 8/2004 | Schneiderbauer |
| 6,783,117 B2 | 8/2004 | Wohrle |
| 6,788,011 B2 | 9/2004 | Mueller et al. |
| 6,788,344 B2 | 9/2004 | Igarashi |
| 6,792,199 B2 | 9/2004 | Levine et al. |
| 6,801,003 B2 | 10/2004 | Schanberger et al. |
| 6,802,460 B2 | 10/2004 | Hess et al. |
| 6,806,659 B1 | 10/2004 | Mueller et al. |
| 6,810,204 B2 | 10/2004 | Grone et al. |
| 6,811,287 B2 | 11/2004 | Roller et al. |
| 6,813,094 B2 | 11/2004 | Kaminsky et al. |
| 6,819,506 B1 | 11/2004 | Taylor et al. |
| 6,824,296 B2 | 11/2004 | Souza et al. |
| 6,827,286 B2 | 12/2004 | Zobele |
| 6,827,466 B2 | 12/2004 | Tsai |
| 6,829,852 B1 | 12/2004 | Uehran |
| 6,832,794 B2 | 12/2004 | He et al. |
| 6,837,585 B2 | 1/2005 | Roggatz |
| 6,839,506 B2 | 1/2005 | He et al. |
| 6,843,965 B2 | 1/2005 | Matulevich |
| 6,843,969 B1 | 1/2005 | Anno |
| 6,846,098 B2 | 1/2005 | Bourdelais et al. |
| 6,848,795 B2 | 2/2005 | Kaminsky et al. |
| 6,850,697 B2 | 2/2005 | Basaganas Millan |
| 6,854,717 B2 | 2/2005 | Millan |
| 6,857,579 B2 | 2/2005 | Harris |
| D502,540 S | 3/2005 | Cruver, IV et al. |
| 6,862,402 B2 | 3/2005 | Kim |
| 6,864,110 B2 | 3/2005 | Summers et al. |
| 6,869,204 B2 | 3/2005 | Morgan et al. |
| 6,871,794 B2 | 3/2005 | McEwen |
| 6,871,982 B2 | 3/2005 | Homan et al. |
| D504,171 S | 4/2005 | Ibarra et al. |
| 6,883,929 B2 | 4/2005 | Dowling |
| 6,885,811 B2 | 4/2005 | He et al. |
| 6,888,322 B2 | 5/2005 | Dowling et al. |
| 6,889,003 B2 | 5/2005 | Triplett et al. |
| 6,890,642 B2 | 5/2005 | Kaminsky et al. |
| 6,895,177 B2 | 5/2005 | He et al. |
| 6,897,381 B2 | 5/2005 | He et al. |
| 6,897,624 B2 | 5/2005 | Lys et al. |
| 6,899,280 B2 | 5/2005 | Kotary et al. |
| 6,901,215 B2 | 5/2005 | He et al. |
| 6,901,925 B2 | 6/2005 | Coughlin |
| 6,909,840 B2 | 6/2005 | Harwig et al. |
| 6,917,402 B2 | 7/2005 | Hosoda et al. |
| 6,917,754 B2 | 7/2005 | Pedrotti et al. |
| 6,920,282 B2 | 7/2005 | He et al. |
| D508,558 S | 8/2005 | Wolpert et al. |
| 6,923,383 B1 | 8/2005 | Joshi |
| 6,924,233 B1 | 8/2005 | Chua et al. |
| 6,926,435 B2 | 8/2005 | Li |
| 6,931,202 B2 | 8/2005 | Pedrotti et al. |
| 6,933,680 B2 | 8/2005 | Oskorep et al. |
| 6,936,978 B2 | 8/2005 | Morgan et al. |
| 6,938,883 B2 | 9/2005 | Adams et al. |
| 6,945,468 B1 | 9/2005 | Rodriguez et al. |
| 6,946,805 B2 | 9/2005 | Segan et al. |
| 6,950,607 B2 | 9/2005 | Yip et al. |
| 6,953,260 B1 | 10/2005 | Allen |
| 6,953,265 B2 | 10/2005 | Suehiro et al. |
| 6,955,581 B1 | 10/2005 | Liu |
| 6,957,012 B2 | 10/2005 | He et al. |
| 6,965,205 B2 | 11/2005 | Piepgras et al. |
| 6,967,448 B2 | 11/2005 | Morgan et al. |
| 6,969,954 B2 | 11/2005 | Lys |
| 6,975,079 B2 | 12/2005 | Lys et al. |
| 2001/0011779 A1 | 8/2001 | Stover |
| 2001/0032655 A1 | 10/2001 | Gindi |
| 2002/0021892 A1 | 2/2002 | Ambrosi et al. |
| 2002/0036617 A1 | 3/2002 | Pryor |
| 2002/0048169 A1 | 4/2002 | Dowling et al. |
| 2002/0066798 A1 | 6/2002 | Laudamiel-Pellet et al. |
| 2002/0068009 A1 | 6/2002 | Laudamiel-Pellet et al. |
| 2002/0068010 A1 | 6/2002 | Laudamiel-Pellet et al. |
| 2002/0075677 A1 | 6/2002 | Dokupil |
| 2002/0097978 A1 | 7/2002 | Lowry et al. |
| 2002/0105099 A1 | 8/2002 | Warren |
| 2002/0113555 A1 | 8/2002 | Lys et al. |
| 2002/0113912 A1 | 8/2002 | Wright et al. |
| 2002/0136542 A1 | 9/2002 | He et al. |
| 2002/0136886 A1 | 9/2002 | He et al. |
| 2002/0145394 A1 | 10/2002 | Morgan et al. |
| 2002/0159274 A1 | 10/2002 | Hubbell et al. |
| 2002/0172512 A1 | 11/2002 | Stathakis et al. |
| 2002/0195975 A1 | 12/2002 | Schanberger et al. |
| 2003/0012018 A1 | 1/2003 | Kluth |
| 2003/0028260 A1 | 2/2003 | Blackwell |
| 2003/0028888 A1 | 2/2003 | Hunter et al. |
| 2003/0035917 A1 | 2/2003 | Hyman |
| 2003/0057887 A1 | 3/2003 | Dowling et al. |
| 2003/0063902 A1 | 4/2003 | Pedrotti et al. |
| 2003/0076281 A1 | 4/2003 | Morgan |
| 2003/0137258 A1 | 7/2003 | Piepgras et al. |
| 2003/0138241 A1 | 7/2003 | Pedrotti et al. |
| 2003/0147243 A1 | 8/2003 | Alduby |
| 2003/0168524 A1 | 9/2003 | Hess et al. |
| 2003/0168751 A1 | 9/2003 | Bartsch et al. |
| 2003/0169400 A1 | 9/2003 | Buazza et al. |
| 2003/0169513 A1 | 9/2003 | Kaminsky et al. |
| 2003/0169514 A1 | 9/2003 | Bourdelais et al. |
| 2003/0175019 A1 | 9/2003 | Bresolin et al. |
| 2003/0175148 A1 | 9/2003 | Kvietok et al. |
| 2003/0194355 A1 | 10/2003 | Pedrotti et al. |
| 2003/0205364 A1 | 11/2003 | Sauciuc et al. |
| 2003/0206411 A9 | 11/2003 | Dowling et al. |
| 2003/0214080 A1 | 11/2003 | Maki et al. |
| 2003/0222587 A1 | 12/2003 | Dowling et al. |
| 2004/0004839 A1 | 1/2004 | Souza et al. |
| 2004/0007710 A1 | 1/2004 | Roy et al. |
| 2004/0007787 A1 | 1/2004 | Kvietok et al. |
| 2004/0009103 A1 | 1/2004 | Westring |
| 2004/0016818 A1 | 1/2004 | Murdell et al. |
| 2004/0028551 A1 | 2/2004 | Kvietok et al. |
| 2004/0033067 A1 | 2/2004 | He et al. |
| 2004/0033171 A1 | 2/2004 | Kvietok et al. |
| 2004/0035409 A1 | 2/2004 | Harwig et al. |
| 2004/0036006 A1 | 2/2004 | Dowling |
| 2004/0044106 A1 | 3/2004 | Portnoy et al. |
| 2004/0076410 A1 | 4/2004 | Zobele et al. |
| 2004/0090191 A1 | 5/2004 | Mueller et al. |
| 2004/0090787 A1 | 5/2004 | Dowling et al. |
| 2004/0095746 A1 | 5/2004 | Murphy |
| 2004/0105261 A1 | 6/2004 | Ducharme |
| 2004/0105264 A1 | 6/2004 | Spero |
| 2004/0105669 A1 | 6/2004 | He et al. |
| 2004/0113568 A1 | 6/2004 | Dowling et al. |
| 2004/0130909 A1 | 7/2004 | Mueller et al. |

| | | |
|---|---|---|
| 2004/0131509 A1 | 7/2004 | He et al. |
| 2004/0141315 A1 | 7/2004 | Sherburne |
| 2004/0141321 A1 | 7/2004 | Dowling et al. |
| 2004/0144884 A1 | 7/2004 | He et al. |
| 2004/0145067 A1 | 7/2004 | Millan |
| 2004/0150993 A1 | 8/2004 | McElhaney et al. |
| 2004/0150994 A1 | 8/2004 | Kazar et al. |
| 2004/0155609 A1 | 8/2004 | Lys et al. |
| 2004/0160199 A1 | 8/2004 | Morgan et al. |
| 2004/0178751 A1 | 9/2004 | Mueller et al. |
| 2004/0179167 A1 | 9/2004 | Dahi et al. |
| 2004/0208675 A1 | 10/2004 | Horikoshi et al. |
| 2004/0212993 A1 | 10/2004 | Morgan et al. |
| 2004/0235430 A1 | 11/2004 | Ma et al. |
| 2004/0240890 A1 | 12/2004 | Lys et al. |
| 2004/0247300 A1 | 12/2004 | He et al. |
| 2004/0249094 A1 | 12/2004 | Demain |
| 2004/0257007 A1 | 12/2004 | Lys et al. |
| 2005/0002105 A1 | 1/2005 | Nemoto et al. |
| 2005/0024868 A1 | 2/2005 | Nagai et al. |
| 2005/0029688 A1 | 2/2005 | Hagmann et al. |
| 2005/0030744 A1 | 2/2005 | Ducharme |
| 2005/0035728 A1 | 2/2005 | Schanberger et al. |
| 2005/0036300 A1 | 2/2005 | Dowling et al. |
| 2005/0040774 A1 | 2/2005 | Mueller et al. |
| 2005/0041161 A1 | 2/2005 | Dowling et al. |
| 2005/0041424 A1 | 2/2005 | Ducharme |
| 2005/0044617 A1 | 3/2005 | Mueller et al. |
| 2005/0047132 A1 | 3/2005 | Dowling et al. |
| 2005/0047134 A1 | 3/2005 | Mueller et al. |
| 2005/0053368 A1 | 3/2005 | Pesu et al. |
| 2005/0053528 A1 | 3/2005 | Rymer |
| 2005/0062440 A1 | 3/2005 | Lys et al. |
| 2005/0063194 A1 | 3/2005 | Lys et al. |
| 2005/0068777 A1 | 3/2005 | Popovic |
| 2005/0069304 A1 | 3/2005 | He et al. |
| 2005/0069306 A1 | 3/2005 | He et al. |
| 2005/0069307 A1 | 3/2005 | He et al. |
| 2005/0099824 A1 | 5/2005 | Dowling et al. |
| 2005/0105186 A1 | 5/2005 | Kaminsky et al. |
| 2005/0105296 A1 | 5/2005 | French |
| 2005/0105303 A1 | 5/2005 | Emde |
| 2005/0116667 A1 | 6/2005 | Mueller et al. |
| 2005/0117365 A1 | 6/2005 | Menke |
| 2005/0122065 A1 | 6/2005 | Young |
| 2005/0122292 A1 | 6/2005 | Schmitz et al. |
| 2005/0122721 A1 | 6/2005 | Hori |
| 2005/0122722 A1 | 6/2005 | Menke |
| 2005/0128743 A1 | 6/2005 | Chuey et al. |
| 2005/0128751 A1 | 6/2005 | Roberge et al. |
| 2005/0133617 A1 | 6/2005 | Hidalgo et al. |
| 2005/0146893 A1 | 7/2005 | Ford et al. |
| 2005/0147523 A1 | 7/2005 | Laudamiel-Pelleet et al. |
| 2005/0147539 A1 | 7/2005 | Laudamiel-Pellet et al. |
| 2005/0151489 A1 | 7/2005 | Lys et al. |
| 2005/0157499 A1 | 7/2005 | Kim |
| 2005/0167522 A1 | 8/2005 | Wheatley et al. |
| 2005/0168986 A1 | 8/2005 | Wegner |
| 2005/0174473 A1 | 8/2005 | Morgan et al. |
| 2005/0174777 A1 | 8/2005 | Cooper et al. |
| 2005/0178345 A1 | 8/2005 | Crapser |
| 2005/0180736 A1 | 8/2005 | Zobele |
| 2005/0185392 A1 | 8/2005 | Walter et al. |
| 2005/0185395 A1 | 8/2005 | Pinter |
| 2005/0191481 A1 | 9/2005 | He et al. |
| 2005/0194460 A1 | 9/2005 | Selander |
| 2005/0195598 A1 | 9/2005 | Dancs et al. |
| 2005/0196159 A1 | 9/2005 | Zobele |
| 2005/0201107 A1 | 9/2005 | Seki |
| 2005/0201944 A1 | 9/2005 | Kvietok et al. |
| 2005/0205916 A1 | 9/2005 | Conway et al. |
| 2005/0211790 A1 | 9/2005 | Kvietok et al. |
| 2005/0212404 A1 | 9/2005 | Chen et al. |
| 2005/0213352 A1 | 9/2005 | Lys et al. |
| 2005/0213353 A1 | 9/2005 | Lys et al. |
| 2005/0214158 A1 | 9/2005 | Kvietok et al. |
| 2005/0218243 A1 | 10/2005 | Zobele et al. |
| 2005/0218838 A1 | 10/2005 | Lys et al. |
| 2005/0218870 A1 | 10/2005 | Lys et al. |
| 2005/0219838 A1 | 10/2005 | Belliveau |
| 2005/0219872 A1 | 10/2005 | Lys et al. |
| 2005/0225856 A1 | 10/2005 | Kokuzawa et al. |
| 2005/0226788 A1 | 10/2005 | Hrybyk et al. |
| 2005/0231133 A1 | 10/2005 | Lys et al. |
| 2005/0232831 A1 | 10/2005 | Taylor et al. |
| 2005/0236029 A1 | 10/2005 | Dowling |
| 2005/0236998 A1 | 10/2005 | Mueller et al. |
| 2005/0248299 A1 | 11/2005 | Chemel et al. |
| 2005/0253533 A1 | 11/2005 | Lys et al. |
| 2005/0275626 A1 | 12/2005 | Mueller et al. |
| 2005/0276053 A1 | 12/2005 | Nortrup |
| 2005/0285547 A1 | 12/2005 | Piepgras |
| 2006/0002110 A1 | 1/2006 | Dowling et al. |
| 2006/0012987 A9 | 1/2006 | Ducharme |
| 2006/0016960 A1 | 1/2006 | Morgan et al. |
| 2006/0193611 A1 | 8/2006 | Ruiz Ballesteros et al. |
| 2006/0231213 A1 | 10/2006 | Matsuda et al. |
| 2006/0280659 A1 | 12/2006 | Brown et al. |

FOREIGN PATENT DOCUMENTS

| | | |
|---|---|---|
| DE | 3701499 | 7/1988 |
| DE | 4131613 | 3/1993 |
| DE | 4446413 | 12/1994 |
| DE | 296 08 454 | 9/1996 |
| EP | 0 252 642 | 1/1988 |
| EP | 0537130 B1 | 4/1993 |
| EP | 0548274 B1 | 6/1993 |
| EP | 0617667 A1 | 10/1994 |
| EP | 0705281 A1 | 4/1996 |
| EP | 0736248 A1 | 10/1996 |
| EP | 0945062 B1 | 9/1999 |
| EP | 0956868 B1 | 11/1999 |
| EP | 1 033 139 | 9/2000 |
| EP | 1 219 308 | 7/2002 |
| EP | 1332765 A1 | 8/2003 |
| EP | 1422249 A1 | 5/2004 |
| ES | 1005422 | 11/1988 |
| ES | 1015255 | 6/1991 |
| GB | 2277267 A | 10/1994 |
| GB | 2369816 A | 6/2002 |
| GB | 2 399 643 | 9/2004 |
| JP | 54-21247 | 2/1979 |
| JP | 62094169 | 4/1987 |
| JP | 1295808 | 11/1989 |
| JP | 2078077 | 3/1990 |
| JP | 2138577 | 5/1990 |
| JP | 2242633 | 9/1990 |
| JP | 3240701 | 10/1991 |
| JP | 5003744 | 1/1993 |
| JP | 6003627 | 1/1994 |
| JP | 06-36643 | 5/1994 |
| JP | 6155489 | 6/1994 |
| JP | 6205929 | 7/1994 |
| JP | 06-262057 | 9/1994 |
| JP | 07-009744 | 2/1995 |
| JP | 7230847 | 8/1995 |
| JP | 08-084551 | 4/1996 |
| JP | 08-241039 | 9/1996 |
| JP | 8278413 | 10/1996 |
| JP | 09-074971 | 3/1997 |
| JP | 9107861 | 4/1997 |
| JP | 308422 | 12/1997 |
| JP | 10014467 | 1/1998 |
| JP | 10057464 | 3/1998 |
| JP | 2004057548 | 2/2004 |

| | | |
|---|---|---|
| JP | 2004275371 | 10/2004 |
| WO | WO 85/00301 | 1/1985 |
| WO | WO 91/15249 | 10/1991 |
| WO | WO 96/04021 | 2/1996 |
| WO | WO 97/13539 | 4/1997 |
| WO | WO 98/19526 | 5/1998 |
| WO | WO 98/58692 | 12/1998 |
| WO | WO 01/43785 A1 | 6/2001 |
| WO | WO 01/79752 | 10/2001 |
| WO | WO 03/028775 | 4/2003 |
| WO | WO 03/077962 | 9/2003 |
| WO | WO 03098971 A1 | 11/2003 |
| WO | WO 2004071935 A2 | 8/2004 |
| WO | WO 2005/030276 | 4/2005 |
| WO | WO 2005/092400 | 10/2005 |

OTHER PUBLICATIONS

European Search Report, Appl. No. EP 04709400.8, dated Oct. 4, 2006.

* cited by examiner

SYSTEM FOR DETECTING A CONTAINER OR CONTENTS OF THE CONTAINER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to detection systems, and more particularly, to detection systems that can detect an absent or empty container in a diffuser.

2. Description of the Background of the Invention

A multitude of liquid active material emitting devices or diffusers exist in the marketplace. Many of such devices are passive devices that require only ambient air flow to disperse the liquid active material therein. Other devices have a cord and plug extending from the device, a plug extending directly from the device, or batteries, to power elements of the device. In devices having a heater, fan, or other active emitting unit, the user often has no indication that a liquid active material container therein is absent or empty, and therefore the device and its components remain active.

Others have attempted to detect an almost empty condition in a bag or bottle by measuring the capacitance of the contents in the bag or bottle. One such device is attached to a bag or bottle and detects a liquid level of the bag or bottle by detecting a change in capacitance thereof. When the liquid level falls below a specific liquid level, an alarm is generated to signal a user of the condition. Another invention has a capacitance-type fluid level sensor for I.V. and catheter bags. The sensor has conductive plates disposed on an outer surface of a bag to detect a variation in the capacitance of the fluid. When a variation is detected, a comparator determines the level of the fluid. If the fluid is below a threshold level, an alarm signal is provided to an alarm driver.

Another device that detects liquid by measuring the capacitance thereof is an apparatus for detection of liquid incendiaries. The apparatus has a sling supported by first and second supports, wherein two copper strips connected by a conducting wire are attached to the sling. A bottle having contents therein that function as a dielectric medium of a capacitor is disposed in the sling between and in contact with the copper strips. The capacitance of the apparatus changes based on the contents of the bottle, wherein an output signal is generated to indicate the capacitance. When the output signal reaches a predetermined threshold voltage, a light emitting diode (LED) is illuminated.

Other devices use light emitters and light detectors to detect a fluid level in a container. One such device has a light emitter, a light detector disposed adjacent one another near an opening of a container, and a fluid level detector having a light conduit portion, a base surrounding the light conduit portion, two paddles moveably attached to opposite sides of the base, and a biasing member extending between the paddles. Light is emitted through the conduit in the opening and into the container. A reflector disposed on the biasing member reflects the light back through the conduit to the light detector. When the container is full, the biasing member and paddles are biased outwardly. As the container empties, the container begins to collapse, which causes the biasing member and paddles to move inwardly toward one another. Therefore, the reflector is moved away from the conduit, emitter, and detector, thereby varying a path of the light, and thus the intensity of the light received by the detector. The intensity of the light received by the detector is used as an indicator of a fluid amount in the container.

Another device for emitting and controlling the release of volatile materials having an article containing volatile disposed therein has a mechanism that communicates information from the article to the device. The mechanisms have: electrical contacts on or in the article that are capable of being read by electrical circuitry in the device, conductive labeling on or in the article that mates with contacts associated with the device, optical mechanisms including bar coding on the article being read by the device, changes in topography on the article that are capable of being read by sensors in the device, or a radio frequency (RF) identification tag on or in the article that communicates with the device.

SUMMARY OF THE INVENTION

According to one aspect of the present invention, a system for detecting a container or contents of the container comprises a diffuser for retaining the container, wherein the container is configured to hold an active material therein and includes a wick extending therefrom. The system further includes a sensor positioned to detect at least one of the container retained in the diffuser and the contents of the container retained in the diffuser.

According to another aspect of the present invention, a system for detecting a container or contents of the container comprising a diffuser for retaining the container, wherein the container is configured to hold an active material therein. The system further includes an emitter disposed adjacent the container and a receiver disposed adjacent the container. The emitter and receiver are operatively connected to detect at least one of the container retained in the diffuser and the contents of the container retained in the diffuser.

According to yet another aspect of the present invention, a system for detecting a container or contents of the container comprises a diffuser for retaining the container, wherein the container is configured to hold an active material therein and includes a wick extending therefrom. The system further includes an emitter disposed adjacent the wick and a receiver disposed adjacent the wick. The emitter and receiver are operatively connected to detect at least one of the container retained in the diffuser and the contents of the container retained in the diffuser.

According to still another aspect of the present invention, a system for detecting a container or contents of the container comprises a diffuser for retaining the container, wherein the container is configured to hold an active material therein and includes a wick extending therefrom. The system further includes a capacitance element disposed adjacent the wick and a capacitance sensor for sensing a change in capacitance of the capacitance element.

Other aspects and advantages of the present invention will become apparent upon consideration of the following detailed description and the attached drawings, in which like elements are assigned like reference numerals.

DETAILED DESCRIPTION OF THE INVENTION

Figure 1:
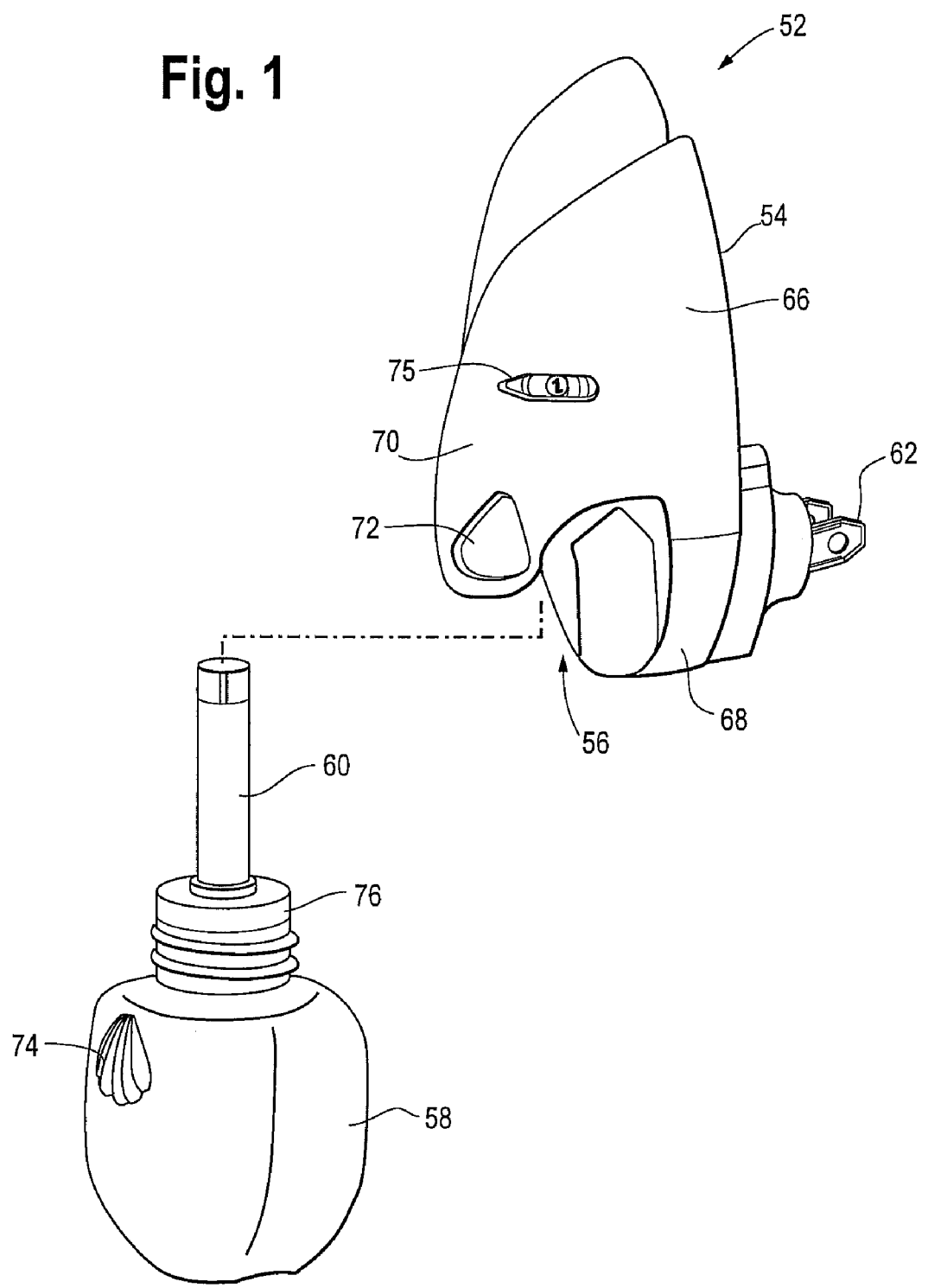
FIG. 1 a perspective view of a diffuser.
Figure 2:
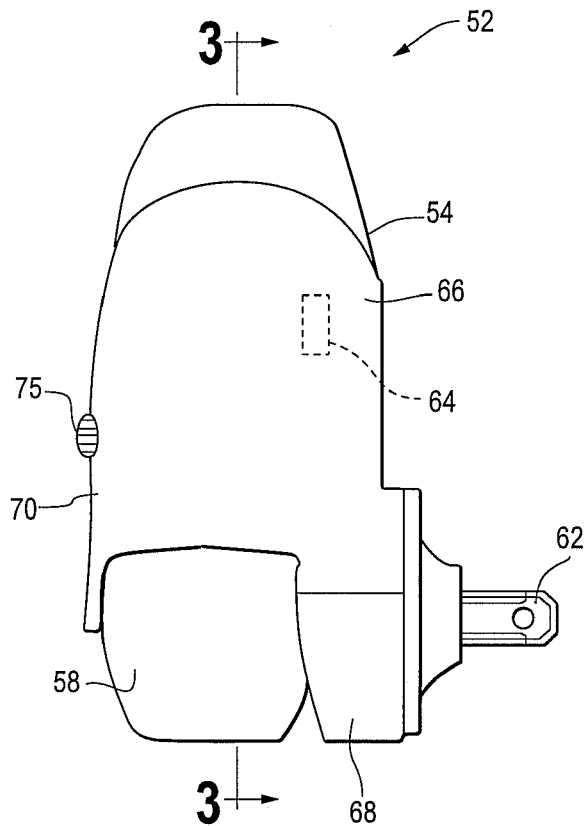
FIG. 2 is a side view of the diffuser of FIG. 1.

FIGS. 1 and 2 illustrate a diffuser 52 generally comprising a housing 54 having a compartment 56 configured to receive and releasably hold a container 58 of active material having a wick 60 extending therefrom, and an electrical plug 62 for connecting the diffuser 52 to a power source. In one embodiment of the present invention, the active material is a liquid active material, but may also be a solid, semi-solid, gel-like, or combinations thereof. The diffuser also may have a heating element 64 to enhance the diffusion of the active material in the container 58.

Illustratively, the housing 54 is made of a thermoplastic material and is injection molded, although the housing 54 may be made of any other suitable material. As seen in FIGS. 1 and 2, the housing 54 includes an upper portion 66 and a lower portion 68 that are fastened together by heat-staking or any other suitable fastening means, including, for example, rivets, press fit, snap fit, screws, ultrasonic welding, adhesives, or the like and combinations thereof. The upper portion 66 substantially forms the compartment 56 into which the container 58 is inserted. A front surface 70 of the upper portion 66 of the housing has an opening 72 that engages a raised pattern 74 on the container 58 to releasably hold the container 58 in place in the housing 54 during use. The front surface 70 of the upper portion 66 of the housing 54 is sufficiently pliant so that pulling the container 58 in a downward direction causes the raised pattern 74 to release from the opening 72 in the front surface 70, thereby enabling removal of the container 58 from the diffuser 52. Optionally, the diffuser 52 may include an adjustment mechanism 75 for moving the wick 60 toward and away from the heater 64, thereby increasing and decreasing, respectively, the amount of liquid active material that is volatilized. Alternatively, a neck portion 76 of the container 58 may be designed, for example, to snap to, or screw into, the housing 54. Suitable containers are available in a wide variety of liquid formulations from S.C. Johnson & Son, Inc., of Racine, Wis., under the GLADE® PLUGINS® SCENTED OILS® and RAID® brand names.

In one embodiment of the present invention, the heating element 64 is a metal oxide resistor potted in a ceramic block, which is capable of handling up to at least about 5 W. One suitable resistor is a 6 kΩ resistor, capable of handling 5 W. Alternatively, the heating element 64 may comprise any other suitable type of heating device, such as a resistance heater, a wire-wound heater, a positive temperature coefficient (PTC) heater, or the like, and combinations thereof.

The plug 62 may be disposed in either the upper or lower portion 66, 68, of the housing 54, and/or may be configured as a separate element that is interposed between the upper and lower portions 66, 68 of the housing during assembly. Illustratively, the plug 62 is secured to the housing 54 in a manner that allows the plug 62 to rotate relative to the housing 54, in order to support the diffuser 52 in an upright position in both horizontal and vertical wall outlets.

Optionally, the diffuser 52 may include a wick adjustment mechanism as described in, for example, U.S. Patent Application Publication No. 2003/0138241 A1, which is hereby incorporated by reference.

A wick of the present invention may be of any desired wick material, such as, for example, a porous/sintered plastics or polymers, such as ultra-density or ultra-high-density polyethylene and polypropylene, bonded fibers, glass sintered fibers, ceramic materials, carbon fibers, sintered carbon, wood, metal foams, compressed wood composites, bundled fibers, woven material fibers, natural fibers, synthetic fibers, and the like. Examples of natural fibers useful in the present invention include cotton and linen. Examples of synthetic fibers useful in the present invention include nylon, polypropylene, polyethylene, polyesters, polyamides, rayon, and polyacetates. Examples of wick materials useful in the present invention are described in, for example, U.S. Patent Publication No. 2002/0136886. One consideration in the selection of the wick material used in a diffuser of the present invention is the temperature required for the volatilization of the active material selected and the temperature tolerance of the wick material. For example, ceramic has a high temperature tolerance, while natural fibers generally have a lower temperature tolerance. The ability to tailor pore size to address wicking rates and fouling is also a consideration when selecting the wick material. Mixtures and combinations of the above wick materials may also be used in the present invention. A container of the present invention may also include one or more wicks of the same or different wick material. Optionally, the wick of the present invention may be surrounded by a plastic shield to protect components of the diffuser from contact with the liquid active material contained in the wick.

As seen in FIGS. 3-7, a first embodiment of the detection system of the present invention as incorporated into the diffuser 52 of FIGS. 1 and 2 includes a light emitter 80 and a light receiver 82 disposed on opposite sides of the wick 60 that extends from the container 58. Illustratively, the light emitter 80 is an LED, but may also be any other lighting element that produces infrared, ultraviolet, red light, and/or visible light. Optionally, the light emitter 80 may be a modulated light source and/or may be a colored LED. An example of a suitable LED is a red LED modulated at 10 kHz with a model number L7113SECH from Kingbright Corporation of Taipei, Taiwan. Selection of the light emitter may depend on many factors, including, but not limited to, the necessary luminous intensity, the necessary viewing angle, the light emitter size, the desired color, the desired wavelength, the distance or placement of the light emitter within the diffuser, the electronics circuitry and/or functionality used in the diffuser, and/or any other relevant factors. In this embodiment, the light receiver 82 is a phototransistor, but may also be any other light receiving element that is sensitive to and/or can detect and/or receive infrared, ultraviolet, red light, and/or visible light, including a photodiode. An example of a suitable phototransistor is a phototransistor sold under model number PT928-6C by Everlight Electronics Co. Ltd. of Taipei, Taiwan.

Figure 3:
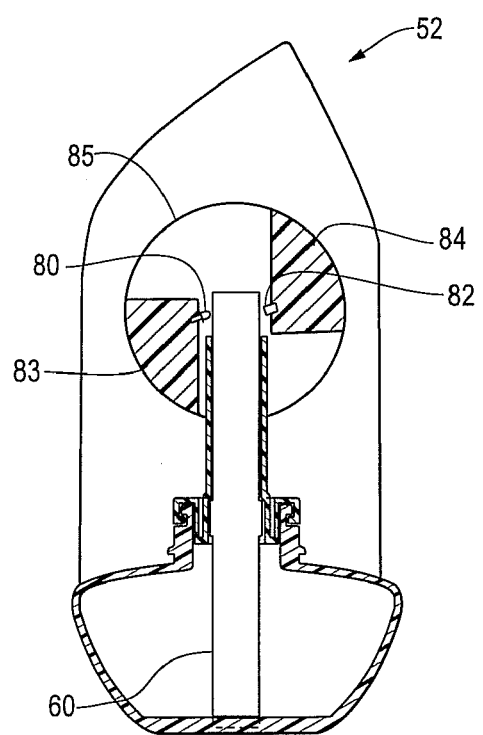
FIG. 3 is a cross-sectional view of the diffuser of FIG. 2 incorporating a container having liquid active material and a detection system therein and taken generally along the lines 3-3 of FIG. 2.

The light emitter 80 and light receiver 82 may be attached to any portion of the diffuser 52 that surrounds the wick 60 and allows the light emitter 80 and light receiver 82 to be disposed in-line with one another. As seen in FIG. 3, the light emitter 80 and light receiver 82 may be attached to first and second portions 83, 84 of a wick centering element 85 disposed in the diffuser 52. The light emitter 80 and light receiver 82 may be attached by any means known in the art. In an example, the light emitter 80 and light receiver 82 (or other components of a detection system) may be attached to a disk-shaped circuit board. The circuit board may be disposed perpendicular to an axis of the wick 60 with the light emitter 80 and light receiver 82 disposed adjacent the wick 60 (or container 58 in the appropriate embodiments). The circuit board is attached to the housing 54 by any means known in the art. For example, the circuit board may be attached to the housing by adhesive, a snap-fit connection, screws, an interference fit, or the like.

Optionally, the light emitter 80 and light receiver 82 may be disposed near a top portion of the wick 60. If a user inserts a container 58 with a short wick 60, or if the user does not fully insert the container 58 into the diffuser 52, the wick 60 may not extend into the path between the light emitter 80 and light receiver 82, and thus, the light transmitted by the emitter 80 is detected directly by the receiver 82. In such scenario, the diffuser 52 may treat this situation as if the container 58 were absent and trigger an event to indicate such condition.

Figure 4:
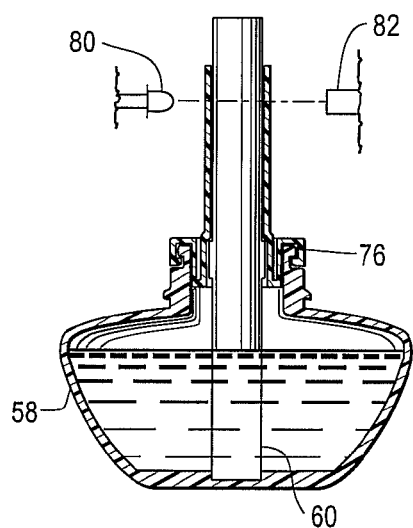
FIG. 4 is a fragmentary cross-sectional view of a container having liquid active material therein and an embodiment of a detection system of FIG. 3 with portions behind the plane of the cross-section omitted for purposes of clarity.
Figure 5:
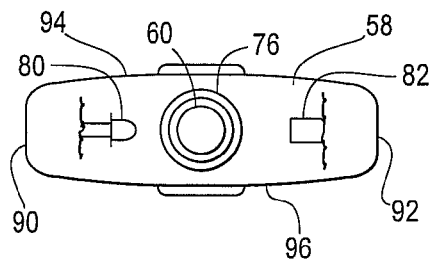
FIG. 5 is a plan view of the embodiment of FIG. 4.

As seen in FIGS. 4 and 5, when the container 58 is full or contains an amount of liquid active material therein, the wick 60 absorbs the liquid active material, thereby allowing the liquid active material to spread throughout the entire wick 60. In such a case, when the liquid active material remains in the container 58 and the wick 60 is wet, light from the light emitter 80 is refracted through the saturated porous wick 60, allowing some light to be detected by the receiver 82. The refractive index of the liquid active material and the material of the wick determine the amount of light from the light emitter 80 that is actually detected by the light receiver 82. For example, in one embodiment, since water has a very low refraction index, if the container 58 has water therein and the wick 60 absorbs water throughout, the light emitted from the light emitter 80 is not refracted through the wick 60 and is therefore not detected by the light receiver 82. Therefore, in one embodiment of the present invention, the liquid active material must have a high enough refractive index to refract light through the wick 60 to ensure that light will be detected by the receiver 82.

Figure 6:
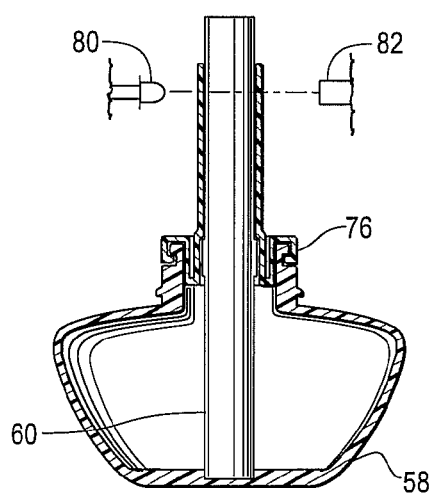
FIG. 6 is a fragmentary cross-sectional view similar to that of FIG. 4, wherein the container is replaced by an empty container.
Figure 7:
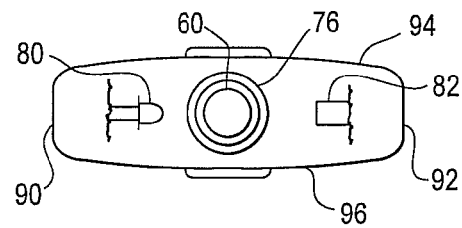
FIG. 7 is a plan view of the embodiment of FIG. 6.

When the container 58 is empty, as seen in FIGS. 6 and 7, the wick 60 does not have any liquid active material to absorb and thus, the wick 60 becomes dry. Generally, a dry state occurs within about seventy-two hours of the liquid active material completely evaporating, but this varies depending on the material used for the wick and the properties of the liquid active material. In this embodiment, when the wick 60 is dry or empty, light from the light emitter 80 enters the dry wick and is reflected into the many cavities of the porous wick 60, with light being absorbed. At some point, the light is no longer transmitted through the wick and therefore does not reach the light receiver 82.

In the embodiment of FIGS. 4-7, if the container 58 and therefore the wick 60 are absent and thus, not inserted into the diffuser 52, light is emitted from the light emitter 80 and received without interruption by the light receiver 82. In this case, the light receiver 82 receives direct light from the light emitter 80 and thus, the light received has a greater intensity than the light received by the receiver 82 when the wick 60 is wet.

As should be evident from the foregoing, in the embodiment of FIGS. 4-7, three different conditions may be present and detectable: an absent container 58, an empty container 58, and a full or partially full container 58. In this embodiment, different signals may be developed for each condition. For example, the receipt of light by the light receiver 82, indicating a full or partially full container 58, may signal the diffuser 52 to operate in its normal fashion. Further, the non-receipt of light by the light receiver 82, indicating an empty container 58, may trigger an event in the diffuser 52 to indicate to the user that the container 58 is absent or empty. For example, non-receipt of light by the light receiver 82 may trigger the device to deactivate the heater 64 (FIG. 2). Optionally or in addition, the diffuser 52 may include an LED indicator on an outer surface thereof that may be activated to indicate that the container 58 is empty. Further, the receipt of high intensity light by the light receiver 82, indicating an absent container 58, may trigger a similar or different event by the diffuser 52.

Optionally, the light receiver 82 of FIGS. 4-7 may be a different type of light receiving device, such as a light pipe. When the container 58 contains liquid active material, the light pipe 82 receives light transmitted by the light emitter 80 and directs the light onto a surface that is visible to the user to indicate that the diffuser is fully functioning. Alternatively, when the container 58 is empty, no light is visible to the user, thereby indicating that the device is not fully functional.

In the embodiments of FIGS. 3-7, the light receiver 82 is disposed close to the wick 60 in order to reduce or minimize the amount of stray light that the receiver 82 might detect and/or to increase or maximize the light intensity to increase the likelihood of the receiver 82 detecting the light from the emitter 80. In an example, the light emitter 80 and the light receiver 82 are potentially both disposed between about 1 mm and about 10 mm from the wick 60, and more preferably between about 2.5 mm and about 7.5 mm from the wick 60, and most preferably about 5 mm from the wick 60. Optionally, the light emitter 80 and/or light receiver 82 may be disposed greater than 10 mm from the wick 60. When the distance between the light emitter 80 and/or light receiver 82 and the wick 60 is greater than 10 mm, a collimator or a light pipe may be employed to focus the light emitted into the wick 60 and the light coming from the wick 60. A collimator may also be used for distances less than 10 mm in order to increase the efficiency of the detection device. Examples of collimators include a narrow tube, a straight or shaped lens, or any other known collimator.

Although in FIGS. 3-7 the light emitter 80 and light receiver 82 are shown disposed adjacent the wick 60 above first and second sides 90, 92 of the container 58, the light emitter 80 and receiver 82 may also be disposed in the same manner adjacent the wick 60 at or near the front and back 94, 96 of the container 58. Alternatively, the light emitter 80 and light receiver 82 may be disposed in any corresponding position surrounding the wick 60, wherein the light emitter 80 and light receiver 82 are on opposite sides of the wick 60.

As seen in FIGS. 8-11, a second embodiment of the detection system of the present invention as incorporated into the diffuser 52 of FIGS. 1 and 2 includes a light emitter 180 and a light receiver 182 disposed around a wick 160 that extends from a container 158. In this embodiment, the light emitter 180 and light receiver 182 are at an approximate right angle to one another, but may also be at any other desirable or suitable angle wherein the light receiver 182 can potentially detect light from the light emitter 180. Also in this embodiment, the light emitter 180 is an LED and the light receiver 182 is a phototransistor, but either may also be any other device that emits or receives light as described herein or known in the art. The LED of FIGS. 8-11 may be slightly offset from a center of the wick 160 so as to avoid partial illumination of the wick 160 in front of the light receiver 182. The light receiver 82 is disposed close to the wick to reduce or minimize receipt of stray light by the receiver 82.

Figure 8:
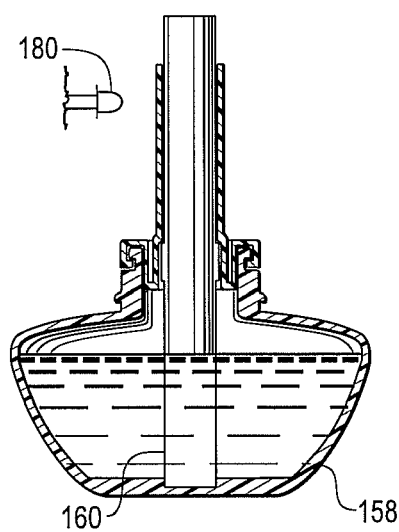
FIG. 8 is a fragmentary cross-sectional view similar to that of FIG. 4 having a container having liquid active material therein and embodying a second embodiment of a detection system, with portions behind the plane of the cross-section omitted for purposes of clarity.
Figure 9:
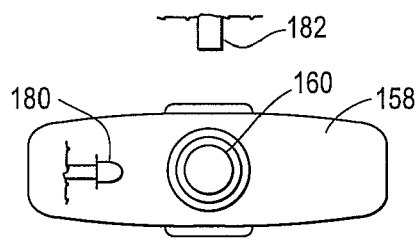
FIG. 9 is a plan view of the embodiment of FIG. 8.
Figure 10:
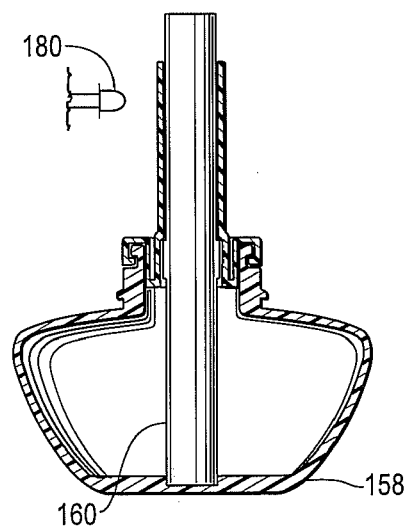
FIG. 10 is a fragmentary cross-sectional view similar to that of FIG. 8, wherein the container is replaced by an empty container.
Figure 11:
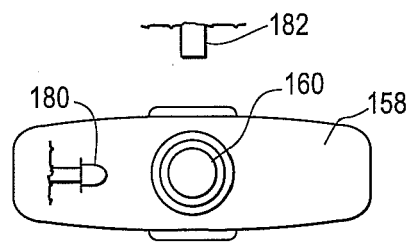
FIG. 11 is a plan view of the embodiment of FIG. 10.

When the container 158, as seen in FIGS. 8 and 9, is full or contains an amount of liquid active material therein, the wick 160 absorbs the liquid active material, thereby allowing the liquid active material to wick or move throughout the entire wick 160. When the wick 160 is wet, light from the light emitter 180 is refracted through cavities of the porous wick 160, thereby allowing some of the light to be detected by the light receiver 182. As seen in FIGS. 10 and 11 when the container 158 is empty, no liquid active is absorbed by the wick 160 and thus, the wick 160 is dry. When the wick 160 is dry, light from the light emitter 180 is absorbed by the wick 160 and therefore does not reach the light receiver 182. Also, when the container 158 and wick 160 are not inserted into the diffuser 52, no light is detected by the receiver 182.

In the embodiment of FIGS. 8-11, the non-receipt of light by the light receiver 182 indicating an absent or empty container 158 may trigger an event in the diffuser 52, as described herein, to indicate to the user that the container 158 is absent or empty.

In an example of the embodiments of FIGS. 8-11, the light emitter 180 and the light receiver 182 are potentially both disposed between about 1 mm and about 10 mm from the container 158, and more preferably between about 2.5 mm and about 7.5 mm from the container 158, and most preferably about 5 mm from the container 158. Optionally, the light emitter 180 and/or light receiver 182 may be disposed greater than 10 mm from the container 158. As in the embodiment of FIGS. 4-7, when the distance between the light emitter 180 and/or light receiver 182 and the container 158 is greater than 10 mm, a collimator or a light pipe may be employed to focus the light emitted into the container 158 and the light coming from the container 158. A collimator may also be used for distances less than 10 mm, in order to increase the efficiency of the detection device. Examples of collimators include a narrow tube, a straight or shaped lens, or any other known collimator.

As with the first embodiment, the light emitter 180 and light receiver 182 of FIGS. 8-11 may be operatively positioned and/or connected in any manner that is suitable for the respective diffuser. For example, the light emitter 180 and light receiver 182 may be disposed at any angle with respect to one another and/or they may both be disposed at any position with respect to the wick 160 and the container 158.

The light emitter 80, 180 and light receiver 82, 182 of FIGS. 3-11 may be disposed near a top portion of the wick 60, 160, such that, if a container 58 having a shorter wick 60, 160 is inserted into the diffuser 52, or if the container 58 is not fully inserted into the diffuser 52, the light emitter 80, 180 and light receiver 82, 182 will not detect the wick 60, 160. In such a situation, the receipt or non-receipt of light by the light receiver 82, 182 may trigger an event in the diffuser 52 similar to that which would indicate an absent container 58, 158.

Figure 12:
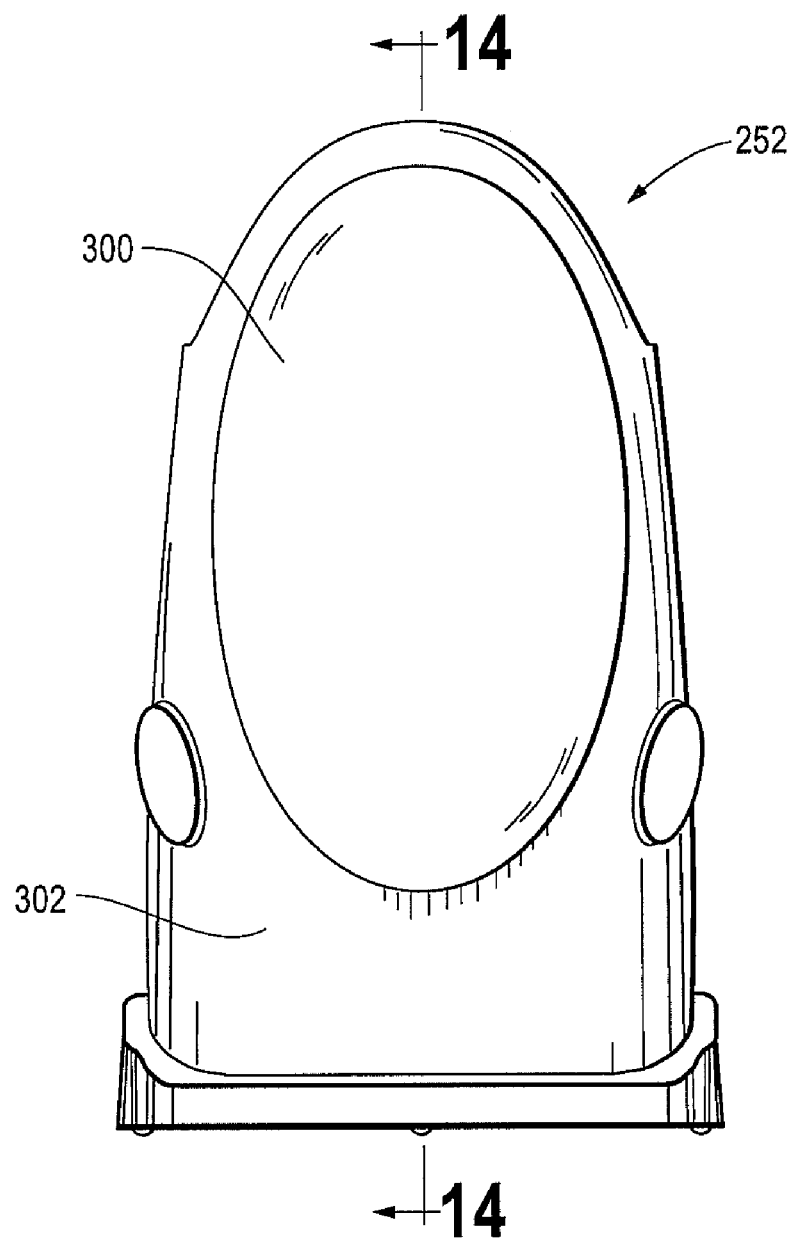
FIG. 12 is a front view of another diffuser of the present invention.
Figure 13:
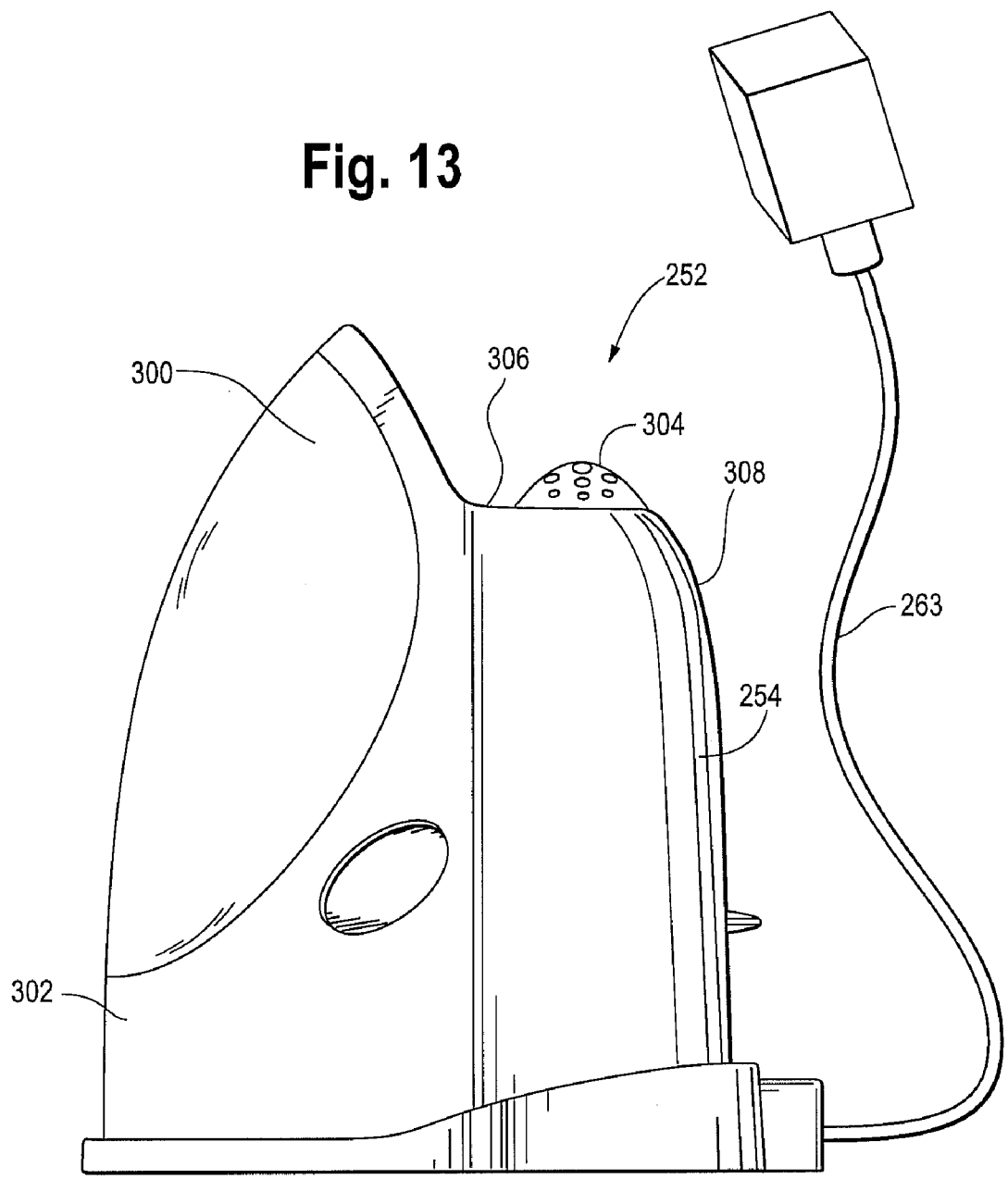
FIG. 13 is a side view of the diffuser of FIG. 12.
Figure 14:
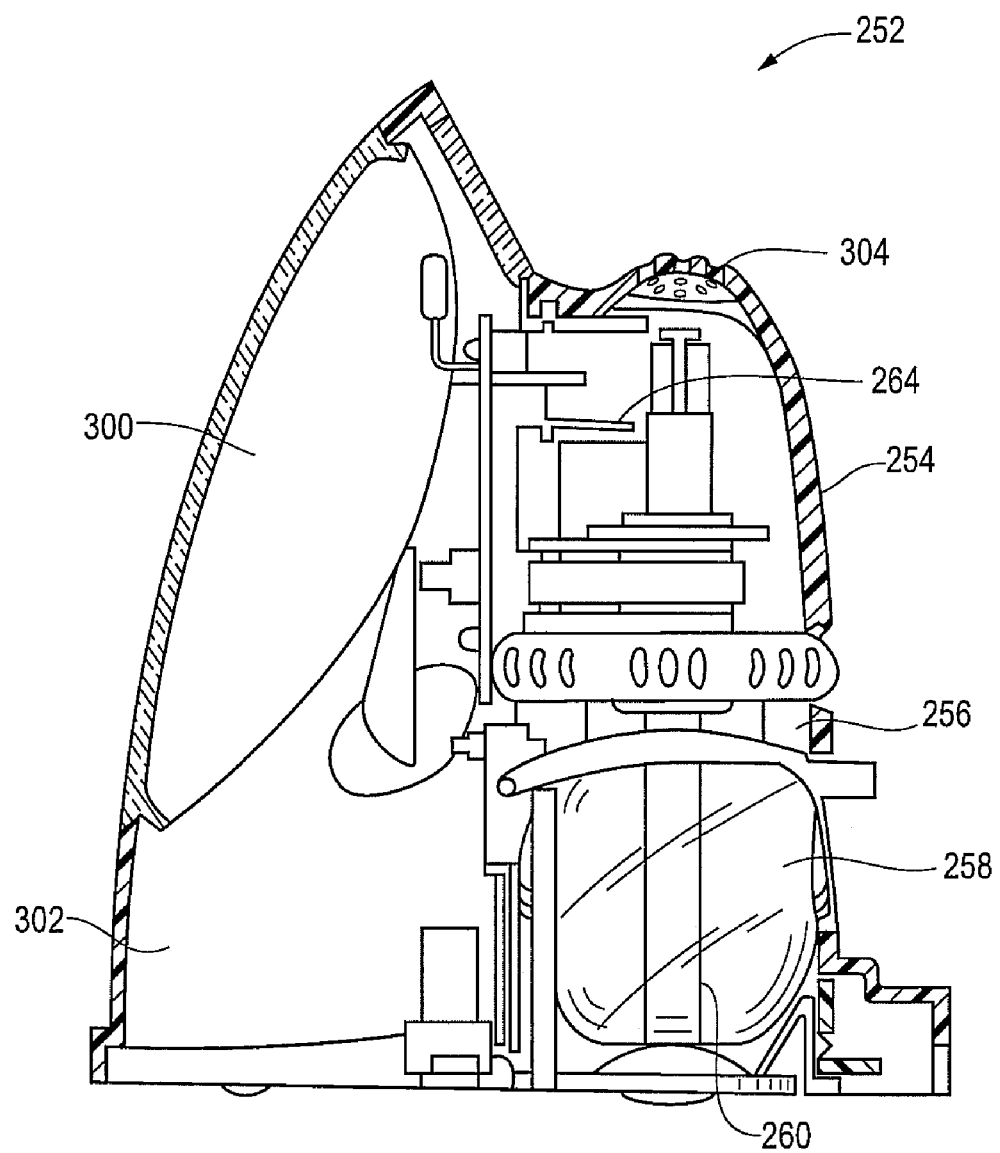
FIG. 14 is a cross-sectional view of the diffuser of FIG. 12 incorporating a container having liquid active material and a detection system therein and taken generally along the lines 14-14 of FIG. 13.

FIGS. 12-14 illustrate a diffuser 252 similar or identical to the other diffuser embodiments disclosed herein and generally comprising a housing 254 having a compartment 256 configured to receive and releasably hold a container 258 of liquid active material having a wick 260 extending therefrom, and an electrical cord and plug 263 for connecting the diffuser 252 to a power source. Still further, the diffuser may also include at least one LED (not shown) for illuminating the surrounding area and at least one lens 300 in a front portion 302 thereof for allowing light from the at least one LED to escape therefrom. The diffuser 252 also may have a heating element 264 as described in detail above, to enhance the diffusion of the active material from the container 258 and one or more vent holes 304 disposed in a top portion 306 and/or a rear portion 308 thereof for dispersion of active material from the diffuser 252.

Figure 15:
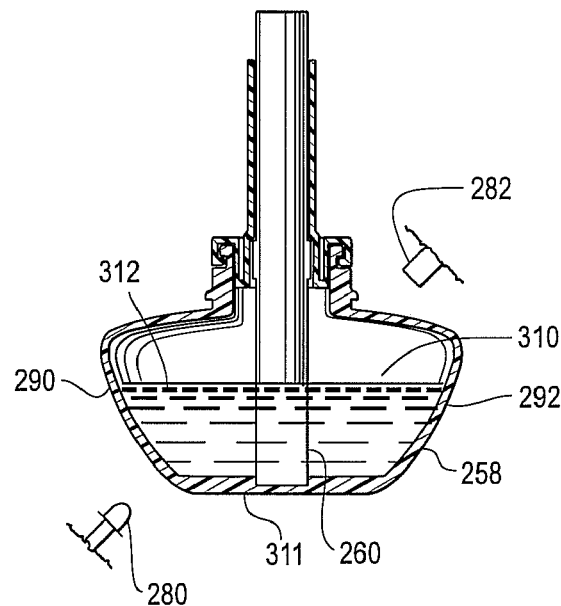
FIG. 15 is a fragmentary cross-sectional view of a container having liquid active material therein and a third embodiment of a detection system, with portions behind the plane of the cross-section omitted for purposes of clarity.
Figure 16:
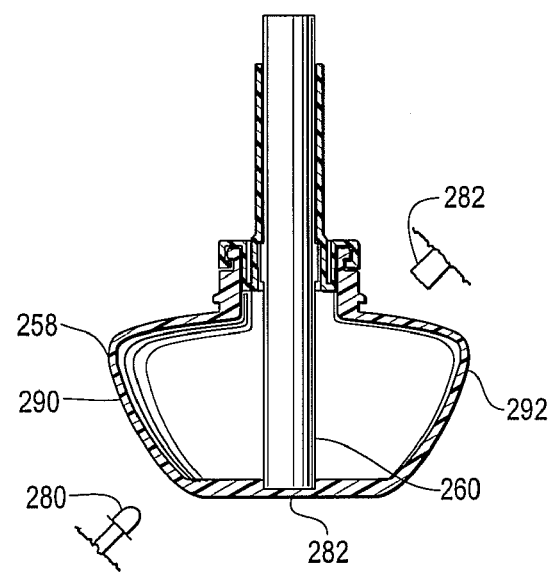
FIG. 16 is a fragmentary cross-sectional view similar to that of FIG. 15, wherein the container is replaced by an empty container.

FIGS. 15 and 16 depict a third embodiment of the detection system of the present invention as incorporated into the diffuser 252 of FIGS. 12-14, although the detection system may be incorporated into any diffuser. The detection system includes a light emitter 280 and a light receiver 282 disposed substantially in line with one another around the container 258 and in light communication with one another through the liquid active material in the container 258. The light emitter 280 is an LED and the light receiver 282 is a phototransistor, but as with other embodiments, any light emitter(s) and/or light receiver(s) known in the art may be employed. If one of the light emitter 280 and the light receiver 282 is positioned above a fill-level 310 of a full container 258 and the other of the emitter 280 or receiver 282 is located at a bottom 311 of the container 258, as seen in FIGS. 15 and 16, an empty state (FIG. 16) of the container 258 may be detected. In this case, the light receiver 282 receives light transmitted from the light emitter 280 when the container 258 is absent or empty. Otherwise, when the light enters the container 258 and reaches a top 312 of the liquid active material, the light is reflected and/or refracted, and thus, does not reach the receiver 282. In either case, the receipt or non-receipt of light by the receiver 282 is indicated to the user with some form of notice that the container 258 is absent or empty.

Figure 17:
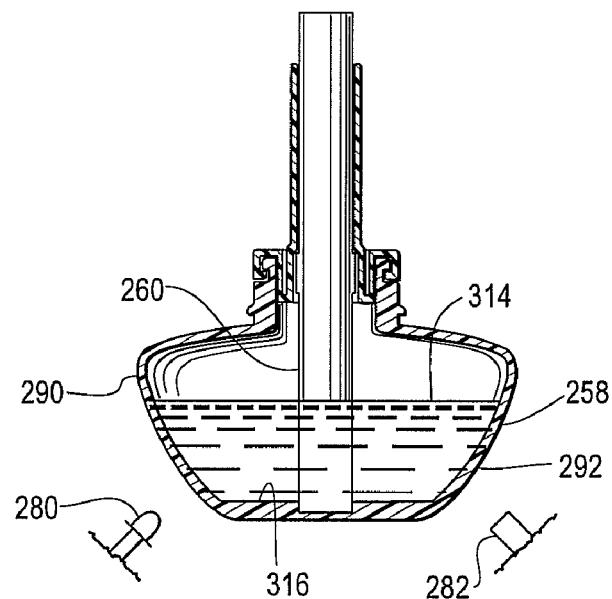
FIG. 17 is a fragmentary cross-sectional view of a container having liquid active material therein and a fourth embodiment of a detection system, with portions behind the plane of the cross-section omitted for purposes of clarity.
Figure 18:
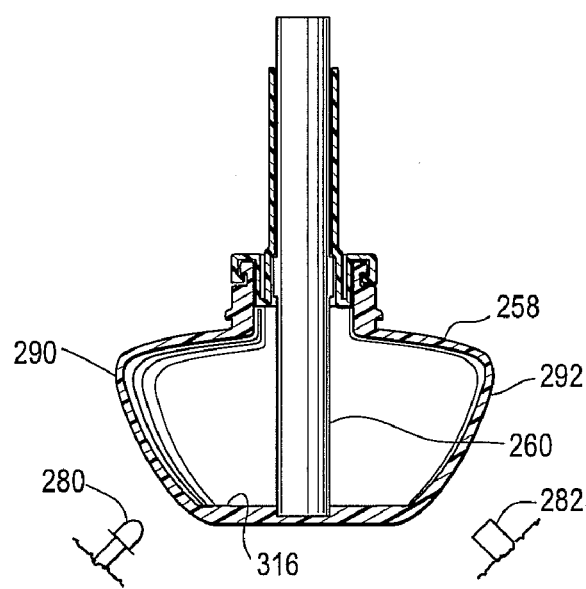
FIG. 18 is a fragmentary cross-sectional view similar to that of FIG. 17, wherein the container is replaced by an empty container.

A fourth embodiment of the detection system of the present invention as incorporated into the diffuser 252 of FIGS. 12-14 and as seen in FIGS. 17 and 18, includes a light emitter 280 and a light receiver 282 disposed around the container 258, but not in-line with one another. When the light transmitted by the light emitter 280 enters a container 258 with an amount of liquid active material therein (FIG. 17), the liquid active material causes the light to bounce around within the liquid active material between a top fluid-air interface 314 and a container 258 bottom interface 316, whereby a portion of the light is detected by the light receiver 282 as it exits the bottom interface 316. Conversely, when the light transmitted by the light emitter 280 enters a container 258 with no liquid active material therein (FIG. 18), the light is transmitted through and out the opposite side of the container 258, thereby never reaching the receiver 282. Similarly, when no container 258 is present, light transmitted by the light emitter 280 is directed in a straight line and never reaches the receiver 282. As with the previous embodiments, the receipt or non-receipt of light by the receiver 282 may trigger an event by the diffuser 252, whereby the condition is indicated to the user.

Figure 19:
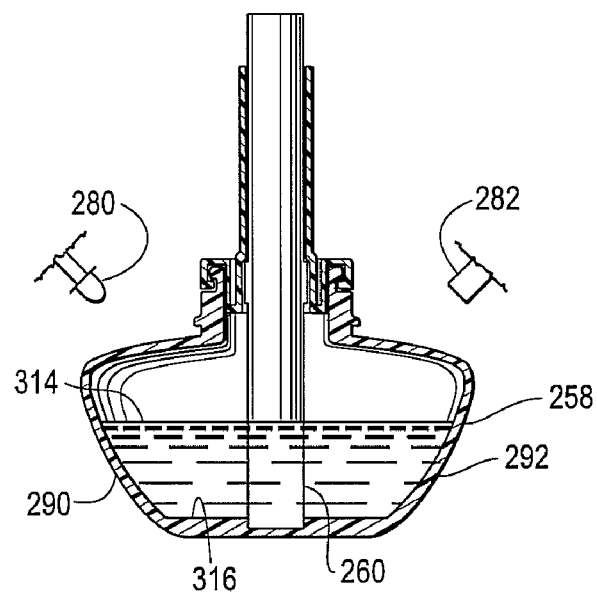
FIG. 19 is a fragmentary cross-sectional view of a container having liquid active material therein and a further embodiment of a detection system, with portions behind the plane of the cross-section omitted for purposes of clarity.
Figure 20:
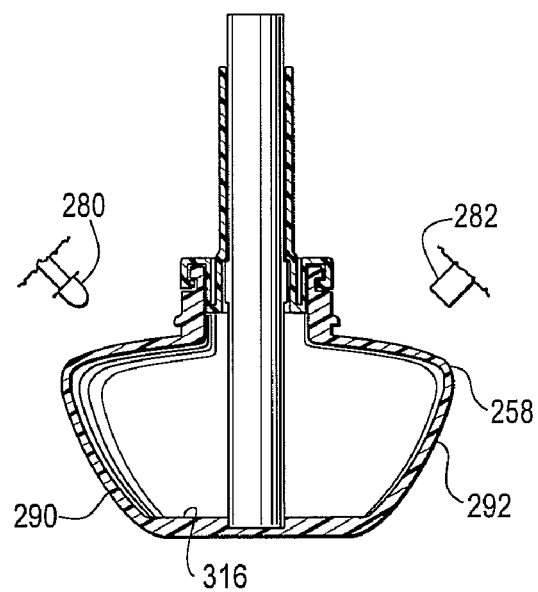
FIG. 20 is a fragmentary cross-sectional view similar to that of FIG. 19, wherein the container is replaced by an empty container.

Yet another embodiment of the detection system of the present invention, similar to those of FIGS. 15-18, as incorporated into any diffuser as described herein or known in the art is depicted in FIGS. 19 and 20. The system includes a light emitter 280 and a light receiver 282 disposed above the container 258 and not in-line with one another. When light is transmitted by the light emitter 280 and enters the container 258 that includes liquid active material therein (FIG. 19), the liquid active material causes the light to bounce around within the liquid active material between a top fluid-air interface 314 and a container 258 bottom interface 316, wherein a portion of the light is detected by the light receiver 282 as it exits the top interface 314. When light is transmitted through the container 258 with no liquid active material therein (FIG. 20), the light does not reach the receiver 282, as discussed above in relation to the embodiment of FIGS. 17 and 18. Again, the receipt or non-receipt of light by the receiver 282 may trigger an event by the diffuser 252 to indicate to a user that a container 258 is absent or empty.

The location of the receiver in the embodiments of FIGS. 15-18 largely determines how and/or when an empty condition is detected and/or triggered by the diffuser. For example, if the receiver is adjacent a bottom portion of the container, the diffuser will generally detect and/or trigger an empty condition when there is no liquid active material left therein. Conversely, if the receiver is spaced between the bottom portion of the container and the top portion of the container, the diffuser will generally detect and/or trigger an empty condition when some small amount of liquid active material remains therein. This can be useful in detecting when the container is almost empty rather than detecting when the container is fully empty. In other embodiments, multiple receivers can be disposed at various locations to indicate various liquid levels and/or an empty container.

In the embodiments of FIGS. 15-18, the container is clear (translucent) or opaque so that light transmitted by the light emitter is allowed to pass through the container and be detected by the light receiver. Optionally, the container may be any other color if it is desirous to, for example, only detect whether the container is absent.

Although the embodiments of FIGS. 15-20 depict the light emitter 280 and light receiver 282 adjacent the container 258 near a first side 290 and a second side 292 of the container 258, the light emitter 280 and the light receiver 282 may also be disposed in the same manner adjacent a front side (not shown) and a back side (not shown) of the container 258. Alternatively, the light emitter 280 and light receiver 282 may be disposed in any relative positions surrounding the container 258, wherein the light emitter 280 and light receiver 282 are either in-line with one another or out of line with one another.

The light emitter of the embodiments of FIGS. 15-20 is driven using about a 8.5 kHz square wave. The drive frequency of the light emitter is not critical and, in fact, the light emitter may receive direct current (meaning full on). The light receiver may be coupled to any suitable detection circuit, such as an AM, FM, phase shift, or direct level measurement circuit. It should be noted that some detection schemes are more robust than others and are less adversely affected by ambient light.

In another embodiment similar to those of FIGS. 15-20, the light emitter and light receiver may be placed on the same surface of the container. In such an embodiment, emitted light travels into liquid active material in the container and bounces off a reflector placed on a surface of the container or adjacent the container. A portion of the light travels through the liquid active material and is received and detected by the light receiver. Optionally, the reflector may be placed on the wick or inside the container.

Figure 21:
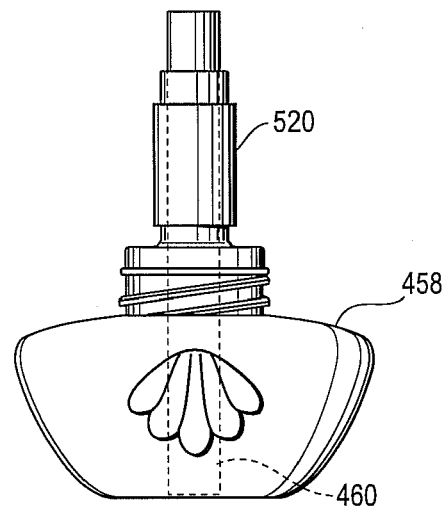
FIG. 21 is a front view of another embodiment of a detection system of the present invention.
Figure 22:
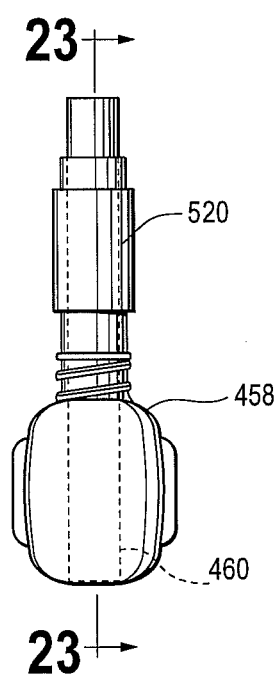
FIG. 22 is a side view of the embodiment of FIG. 21.
Figure 23:
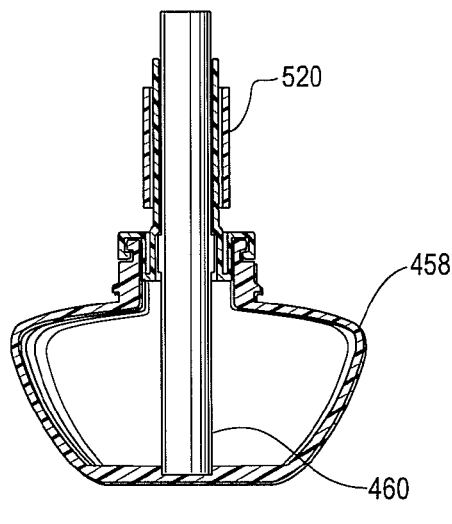
FIG. 23 is a cross-sectional view of the embodiment of FIG. 21 taken generally along the lines 23-23 of FIG. 22, wherein portions behind the plane of the cross-section have been omitted for purposes of clarity.

As seen in FIGS. 21-23, another embodiment of the detection system of the present invention as incorporated into the diffuser 52 of FIGS. 1 and 2, the diffuser 252 of FIGS. 12 and 13, or any other known diffuser, employs an electric field sensor to detect an absent or empty container 458. Illustratively, as seen in FIGS. 21-23, a tubular foil structure 520 is disposed around and surrounds the wick 460 that extends from the container 458. The foil structure 520 is coupled to a suitable excitation and detection circuit. An indication can be generated when a wick is absent, or when a wick is present, but is dry, or when a wet wick is present.

In yet another embodiment of a detection system, one or more metal plates or foils may be disposed adjacent or around the wick. In such embodiment, the plate(s) detects the presence of an induced electrical field. The metal plate may be any kind of metal that is conductive including, but not limited to, copper, gold, aluminum, silver, or any other conductive metals. Optionally, any other conductive material may be utilized. In this embodiment, any object that is conductive and has a different dielectric constant than its surroundings may be sensed by its effect on the electrical field. Using multiple electrodes, the size and shape of the object can be determined.

The electrical field is suitable for detecting objects that are either fixed or in motion within the electrical field.

Figure 24:
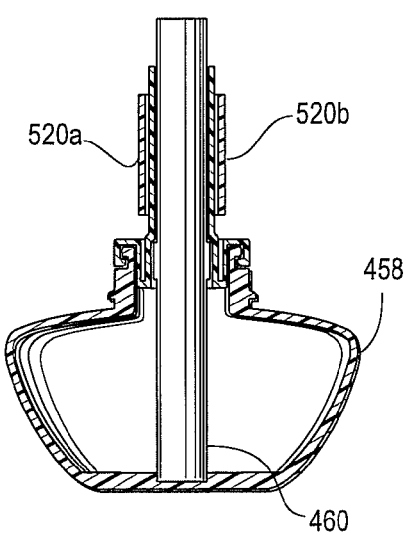
FIG. 24 is a cross-sectional view of a further embodiment, wherein portions behind the plane of the cross-section have been omitted for purposes of clarity.
Figure 25:
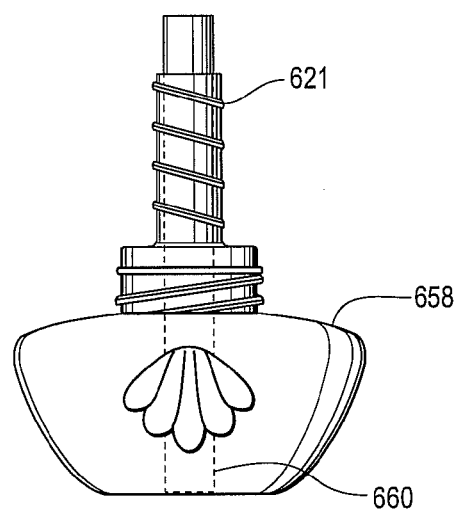
FIG. 25 is a front view of a further embodiment of a detection system of the present invention.

Optionally, as seen in FIG. 24, a capacitance sensor may comprise two straight or curved foil structures 520a, 520b disposed adjacent the wick 460 opposing one another. A capacitance between the foil structures 520a, 520b is continuously measured and differences in the capacitance between the foil structures 520a, 520b are detected. In one embodiment, the capacitance is measured by an oscilloscope probe, but may instead be measured by any other device that measures capacitance and is sized to fit in the respective diffuser. When a dry wick 460 is present adjacent the foil structures 520a, 520b, the capacitance of the foil structures 520a, 520b increases by about five percent from the nominal capacitance of the foil structures 520a, 520b with no wick 460 present. When a wet wick 460 is present adjacent the foil structures 520a, 520b, the capacitance between the foil structures 520a, 520b increases by about twenty percent from the nominal capacitance between the foil structures 520a, 520b. Due to the different capacitance values between the foil structures 520a, 520b with no wick 460, a dry wick 460, and a wet wick 460, different events can be detected and/or triggered by the diffuser 52, 252 for each condition.

Another device that may be utilized to measure the capacitance of a capacitance sensor employs an inductor coupled in parallel with the capacitance sensor to form a tank circuit. In such a circuit, any change in capacitance directly changes the resonant frequency of the circuit. The circuit may be calibrated to detect the difference in frequency between an empty container, an absent container, a container having a wick that is fully saturated with liquid active material, and/or any other suitable conditions. An initial tuning of the circuit to resonance increases the maximum sensitivity to allow for detection of small changes in capacitance.

In the examples of FIG. 24, the foil structures 520a, 520b of the capacitance sensor may be disposed between about 0.5 mm and about 1.5 mm from the wick, and more preferably between about 0.75 mm and about 1.25 mm from the wick, and most preferably about 1.0 mm from the wick.

In a specific example of a capacitance sensor, two sections of foil about 0.900 inch (2.286 cm) in length are disposed opposite one another around the wick with about 0.060 inch (0.152 cm) between the foil sections. One of the foil sections is excited by a 10 volt (peak-to-peak) 16 kHz sine wave and the other foil section is connected to an oscilloscope probe. The nominal capacitance between the foils is about 0.9 pF. A wet wick increases the capacitance to between about 1.1 pF and about 1.4 pF depending on the container and wick geometry. The output voltage is nominally at about 412 mV (zero-to-peak) sine wave, but changes to between about 500 mV and about 635 mV depending on the properties of the wick and the liquid active material.

In a further embodiment of a detection system, as seen in FIG, 25 an electrical coil 621 acting as an inductor may be disposed in a diffuser, such that when a container 658 with wick 660 is inserted into the diffuser, the electrical coil 621 surrounds the wick 660 without contacting the wick 660. This arrangement creates a transformer of sorts, wherein any change in the liquid absorbed by the wick 660 may change the tuned frequency, thereby allowing for differentiation between a container 658 with liquid active material therein and a container 658 with no active liquid material therein.

Figure 26:
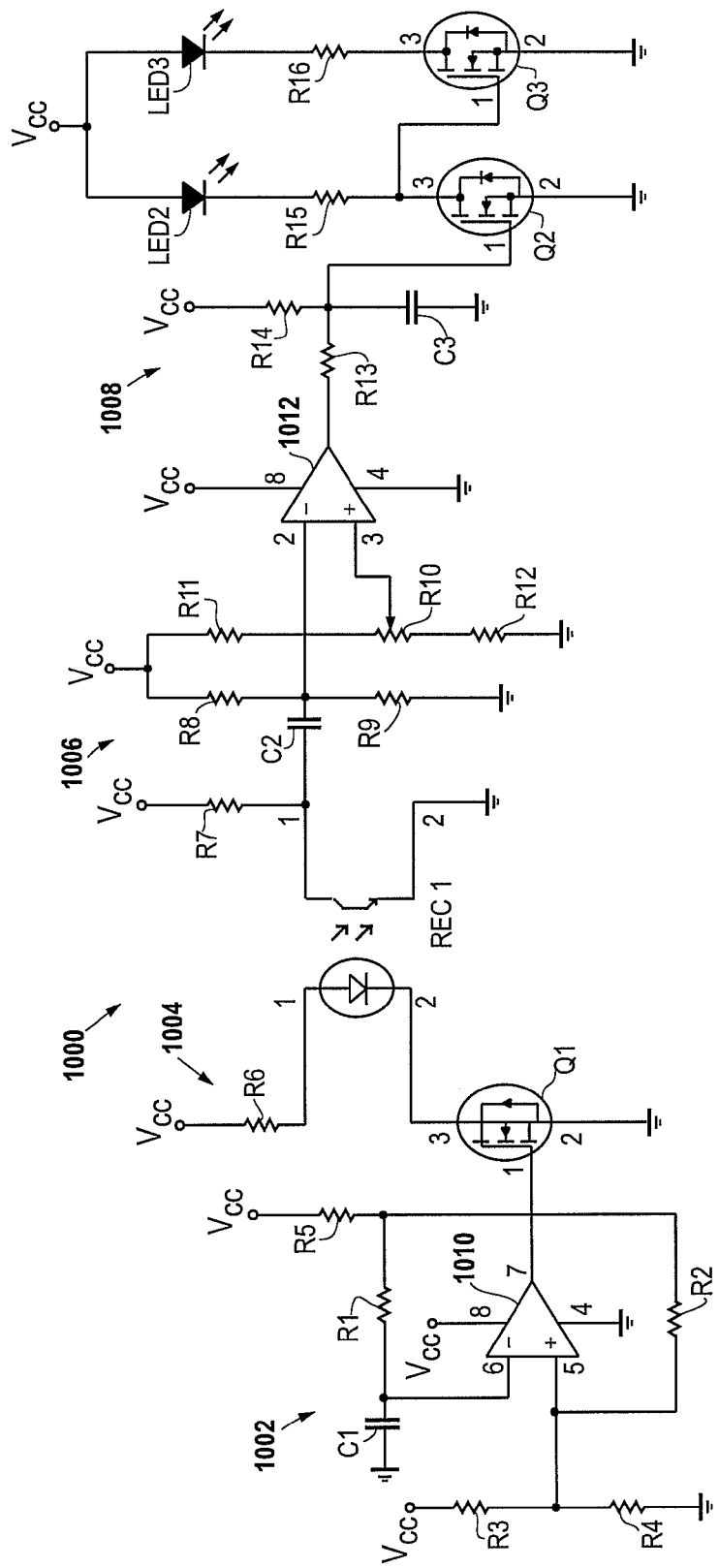
FIG. 26 is a diagram of an exemplary circuit for controlling one or more components of the present invention.

Referring now to FIG. 26, a circuit 1000 for operating any of the embodiments of FIGS. 4-11 and 15-20 is illustrated including a light emitting diode LED1 and an optical transistor REC1 surrounding a wick or a container. The circuit 1000 includes an oscillator section 1002, an LED driver section 1004, a receiver section 1006, and a driver and filter section 1008.

The oscillator section 1002 includes a first op-amp 1010 having an inverting input coupled through a capacitor C1 to ground potential. A resistor R1 is coupled between an output of the op-amp 1010 and the inverting input thereof. A further resistor R2 is coupled between the output of the op-amp 1010 and a non-inverting input thereof. The non-inverting input of the op-amp 1010 is further coupled to a junction between biasing resistors R3 and R4 that are, in turn, coupled between a voltage $V_{cc}$ and ground potential. In addition to the foregoing, a resistor R5 is coupled between the output of the op-amp 1010 and the voltage $V_{cc}$.

The driver section 1004 includes a transistor in the form of a MOSFET Q1 having source and drain electrodes coupled to a cathode electrode of LED1 and ground potential, respectively. A current limiting resistor R6 is coupled between the voltage $V_{cc}$ and an anode terminal of LED1.

The receiver circuit section 1006 includes a resistor R7 coupled between the voltage $V_{cc}$ and a collector electrode of the optical transistor REC1. A drain electrode of the optical transistor REC1 is coupled to ground potential. A capacitor C2 is coupled between the collector electrode of the optical transistor REC1 and an inverting input of a further op-amp 1012. The inverting input of the op-amp 1012 is further coupled to a voltage divider comprising resistors R8 and R9 that are coupled between the voltage $V_{cc}$ and ground potential. A non-inverting input of the op-amp 1012 is coupled through a potentiometer RIO in series with further resistors RM1 and RM2 across the voltage $V_{cc}$ and ground potential.

The driver and filter section 1008 includes a resistor R13 coupled between an output of the op-amp 1012 and a junction between a resistor R14 and a capacitor C3. The resistor R14 and capacitor C3 are coupled across the voltage $V_{cc}$ and ground.

In any of the embodiments disclosed herein, the signal developed at the junction between the resistor R14 and the capacitor C3 may be provided to any suitable indicating device. In the illustrated embodiment, such signal is provided to a gate electrode of a first MOSFET transistor Q2. A drain electrode of the transistor Q2 is coupled to ground potential and a source electrode thereof is coupled to a series combination of a resistor R15 and a light emitting diode LED2. The source electrode of the transistor Q2 is coupled to a gate electrode of the further MOSFET transistor Q3 having a drain electrode coupled to ground potential. A source electrode of the transistor Q3 is coupled through a resistor R16 to a further light emitting diode LED3. Common connected anode electrodes of the LED2 and LED3 are coupled to the voltage $V_{cc}$.

In operation, the oscillator section 1002 produces a square wave at a particular frequency of, for example, 8.5 kHz. This square wave is applied to the gate electrode of the transistor Q1 causing the transistor Q1 to turn on and off at such frequency. The LED1 is thereby energized at a rapid rate with the current therethrough being limited by the resistor R6. When the light produced by the LED1, which may be visible light or infrared light is detected by the optical transistor REC1, the optical transistor REC1 turns on and off at the oscillator frequency, thereby producing an AC waveform at the junction between the resistor R7 and the capacitor C2. The capacitor C2 removes any DC component that may be present in such signal and passes the resulting signal to the inverting input of the op-amp 1012. The op-amp 1012 compares the signal at the inverting input with the DC voltage at the non-inverting input thereof as established by the setting of the potentiometer R10 and the values of the resistances R11 and R12. The result of the comparison is then applied through the RC filter including the resistor R13 and the capacitor C3, which causes a high state signal to be applied to the gate of the transistor Q2. This condition, in turn, causes the transistor Q2 to conduct, thereby causing current to flow through the LED2 and the resistor R15 through the source and drain of the transistor Q2 to ground potential. In addition, the voltage at the source electrode of the transistor Q2 drops to a very low potential (substantially zero volts), in turn causing the transistor Q3 to turn off and preventing current flow through the LED3. Thus, when the light emitted by the LED1 is received by the optical transistor REC1, the LED2 is on and the LED3 is off.

Conversely, when the light developed by LED1 does not reach the optical transistor REC1, no AC signal is produced at the junction between the resistor R7 and the capacitor C2. As a result, the output of the op-amp 1012 is in a low state, thereby turning off the transistor Q2 and allowing the voltage at the gate of the transistor Q3 to rise to a high level. Because the transistor Q3 is a high impedance device, substantially no current flows through the LED2 at this time, and hence LED2 is turned off. Current does flow, however, between the source and drain of the transistor Q3, thereby illuminating LED3.

As should be evident from the foregoing, the circuit shown in FIG. 26 provides a positive indication when light developed by LED1 reaches or does not reach the optical transistor REC1. Thus, in those embodiments of the present invention where reception of light developed by LED1 by the optical transistor REC1 indicates that a wet wick is present, the LED2 is illuminated and the LED3 is off. In such embodiments, when the wick is dry and therefore opaque no light is received by the optical transistor REC1 and hence the LED3 is illuminated and LED2 is off.

In those embodiments where, under the condition that the refill is absent and no light from the LED1 is detected by the optical transistor REC1, the LED3 is illuminated and LED2 is off. In those other embodiments where light developed by LED1 is received by the optical transistor REC1 when the refill is absent, the LED2 is on and LED3 is off.

If desired, the oscillator section 1002 may be replaced by any other suitable apparatus, such as an application-specific integrated circuit (ASIC) or a micro controller or microprocessor. In addition, any of the remaining components of the circuitry of FIG. 26 may be replaced by other suitable circuitry, as desired. For example, the transistors Q2 and Q3, the resistors R15 and R16, and light-emitting diodes LED2 and LED3 may be replaced by a single transistor or multiple transistors that are properly biased to provide a signal to control apparatus that in turn controls any of the components of the diffuser or a signaling apparatus of any suitable type, such as one or more lights, an audible alarm, a combination of lights and audible alarm or the like.

In any of the embodiments incorporating a light emitter and/or a light receiver, a pulsed signal may be transmitted from the light emitter to the light receiver, wherein the signal is an amplitude modulated (AM) signal, a frequency modulated (FM) signal, or a phase shifted signal. A suitable detector is coupled to the receiving device to detect a refill condition.

A collimator may be utilized in any of the embodiments herein that employ a light emitter and/or a light receiver. The collimator in conjunction with a light emitter aids in focusing of the light emitted from the light emitter. When used with a light receiver, the collimator may reduce the effect of ambient light or light coming from other angles or sources, thereby reducing the amount of stray light received by the light receiver.

Any of the embodiments as disclosed herein may include a system for zeroing or negating noise factors, such as temperature, humidity, shock, vibration, customer use, active material spillage onto the sensors, or any other noise factors. The system calibrates the electronics whenever certain conditions exist, for example, when the container is removed from the diffuser. In such example, when the container is removed, the electronics will self-calibrate to zero, thus creating a new baseline so that the diffuser can differentiate between a container with liquid active material therein, an empty container, and a missing container, among the noise factors. An example of a system for activating the software routine would be a mechanical arm that is in contact with the wick. When the container is removed, the arm moves, thereby changing the state of an electrical or optical switch. In another example of a system for zeroing noise factors, an LED is disposed across from the light emitter (in the applicable embodiments) to solely determine the presence of the wick.

In any of the embodiments herein, the detection system may be able to detect whether a foreign object, a container with no wick, and/or a container with a wick having different container or wick dimensions (e.g., height, width, thickness, etc.) is inserted into the diffuser. For example, in a diffuser incorporating a capacitance sensor, the capacitance of the sensor with a shorter wick may produce an undetectable or insignificant change in capacitance of the sensor, therefore indicating that a proper container is not positioned therein. In another example involving a diffuser incorporating a light emitter and light receiver positioned around a wick, the light emitter and light receiver may be positioned such that shorter wicks may not even interrupt light between the light emitter and light receiver.

In order to preserve light emitters and/or light receivers from damage or degradation from the liquid active material and/or other substances, transparent plastic barriers may be disposed between the wick and the light emitter and/or light receiver.

Alternatively, the plastic barrier may be disposed around the light emitter and/or light receiver. The plastic barrier(s) may employ any plastic material that has a high immunity to chemicals, yet still allow transmission of light therethrough.

Illustratively, the liquid active material described herein may be, for example, an insecticide, an insect repellant, an insect attractant, a disinfectant, a mold or mildew inhibitor, a fragrance, a disinfectant, an air purifier, an aromatherapy scent, an antiseptic, an odor eliminator, an air-freshener, a deodorizer, or the like, and combinations thereof, and may be in a liquid, gel, semi-solid and/or solid form.

In one embodiment of the present invention, the diffusers incorporating any embodiment of the detection system of the present invention may include a printed circuit board that may include one or more controllers, memories, and/or processors for controlling the operation of the light emitter, the light receiver and/or the capacitance sensor. The one or more controllers, memories, and/or processors may also control alone or more of the elements of the diffuser (for example, a heater, a light, a timer, etc.) and detect an absent or empty container and trigger the respective event in the diffuser to indicate to the user that the container is absent or empty.

The construction of the diffusers and housings, as described herein, is not critical. In fact, the light emitters, light receivers, and/or sensors of the embodiments as described herein may advantageously be incorporated into the housing of virtually any device that uses a refill or replaceable container, including for example, a diffuser for dispensing fragrance and/or insecticide. Such a device can be found in for example, U.S. Pat. No. 5,647,053. Other devices useful in the present invention include those disclosed in, for example, U.S. Pat. No. 6,706,988. Still other devices useful in the present invention include those disclosed in, for example, U.S. Pat. No. 6,852,403. Further, other devices useful in the present invention include those disclosed in, for example, U.S. Reissue No. 38,150. The devices disclosed in, for example, WO 2004/071935 may also be useful in the present invention, Still other devices useful in the present invention include those found in, for example, U.S. Pat. No. 6,697,571. Other devices useful in the present invention include those disclosed in, for example, U.S. Pat. No. 6,768,865. Further, the device disclosed in, for example, U.S. Pat. No. 6,790,408 may be useful in the present invention. Other devices useful in the present invention include those found in, for example, U.S. Pat. No. 6,854,717. Still further, devices useful in the present invention include those found in, for example, U.S. Pat. No. 6,859,615, This listing of exemplary devices is not meant to be exhaustive.

In any of the embodiments employing a light emitter, in order to conserve power and the light emitter lifetime, the light emitter can be pulsed discontinuously. For example, the light emitter (and the light receiver) might be turned on about every 2 seconds, 5 seconds, 10 seconds, 30 seconds, 1 minute, 5 minutes, 10 minutes, or any other desired or suitable time period. In such case, a timer may be connected to the light emitter and/or light receiver to allow the diffuser to ascertain whether a wick is absent or empty on a discontinuous basis. Pulsing the light emitter discontinuously also reduces the temperature in the light emitter and increases the resistance of the light emitter to the active material. In order to further increase the resistance of the light emitter and also the resistance of the light receiver to the active material, one or both of the light emitter and light receiver may be encased by a translucent housing.

In any of the embodiments described herein, the user may be notified that there is an absent and/or empty container. Such notice might include, for example, deactivating one or more functions of the device, allowing only a single color light to be emitted from the device, deactivating or activating a fan and/or a heater, deactivating or activating a light(s), deactivating or activating a sound or music, deactivating or activating a diffuser element such as a pump, a piezoelectric element, etc., turning the entire diffuser on or off, deactivating or activating a timer, activating a blinking light, activating an alarm, or any other means for notifying the user that a specific condition is present.

Any of the embodiments disclosed herein may include a secondary sensor that is part of the diffuser that may detect a feature on the container. The secondary sensor may be operated at a different frequency, time, and/or wavelength than the primary sensor so as to not interfere therewith. For example, the secondary sensor may be a light emitter, for example an LED, and the feature on the container may be a structure that obstructs or focuses the emitted light from light emitter. If the feature is present on the container, the secondary sensor will detect such feature and trigger an event in the device, such as turning on the diffuser, as described in detail herein. Conversely, if the feature is not present on the container, the secondary sensor will detect that the feature is missing and trigger an event in the device, such as turning off the diffuser, as described in detail herein.

In any of the embodiments as disclosed herein, the light emitter(s), light receiver(s), and/or capacitance sensor(s) may be configured to detect the actual level of the liquid active material. For example, as the container reaches an empty state, the light emitted or capacitance level may decrease, such that this decrease is detectable. This would be useful in detecting a low level of liquid active material in order to convey to the user that the active material is near an empty state.

With any of the embodiments described herein, any number of light emitters, light receivers, and/or capacitance sensors may be employed to detect any absent or empty container.

INDUSTRIAL APPLICABILITY

The present invention provides systems for detecting an absent or empty container within a diffuser. The systems of the present invention may have particular applicability to diffusers that emit fragrances or odor eliminating active materials, as well as insecticide repelling or attracting materials active material. In particular, the systems disclosed herein provided an indication to the user of a diffuser device that a container is absent or empty. Another benefit of the systems of the present invention is that, when there is an absent or empty container, various elements of the diffuser may be deactivated in order to conserve power, battery life, LED life, etc.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. All patents and other references cited herein are incorporated by reference in their entirety. The exclusive rights to all modifications which come within the scope of the appended claims are reserved.

We claim:

1. A system for detecting a container, the system comprising:
    a diffuser for retaining the container, the container configured to hold an active material therein and having a porous wick extending therefrom; and
    a light emitter and a light receiver disposed within the diffuser;
    wherein when active material is present within the porous wick, light emitted by the light emitter is refracted through the wick and at least some of the emitted light is received by the light receiver and, when no active material is present within the porous wick, light emitted by the light emitter enters a dry wick and is absorbed by the wick and none of the emitted light is received by the light receiver.

2. The system claim 1. light emitter and the light receiver are in-line with one another.

3. The system of claim 1 wherein the light emitter is a light emitting diode and the light receiver is a phototransistor.

4. The system of claim 1, wherein the light emitter and the light receiver are disposed adjacent the container when the container is retained in the diffuser.

5. The system of claim 4, wherein the light emitter is a light emitting diode and the light receiver is a phototransistor.

6. A system for detecting a container and contents of the container, the system comprising:
    a diffuser for removably retaining the container, the container configured to hold an active material therein and having a porous wick extending therefrom;
    an emitter disposed outside the container and attached to the diffuser at a position adjacent the wick when the container is disposed within the diffuser; and
    a receiver disposed outside the container and attached to the diffuser at a position adjacent the wick when the container is disposed within the diffuser;

wherein the emitter and the receiver are operatively connected to detect whether the container is disposed in the diffuser and the presence or absence of contents disposed in the container when retained in the diffuser.

7. The system of claim 6, wherein the emitter and receiver are positioned such that when the receiver does not receive a detectable signal from the emitter, an empty condition indicated by the system.

8. The system of claim 6, wherein the emitter and the receiver are aligned with one another such that when the receiver receives a detectable signal from the emitter, at least one of the condition of an absent container or a container having active material therein is indicated by the system.

9. The system of claim 6, wherein the emitter is a light emitting diode and the receiver is a phototransistor.

10. A system for detecting a container, the system comprising:
- a diffuser for removably retaining the container, the container configured to hold an active material therein and having a porous wick extending therefrom;
- an emitter disposed in the diffuser and adjacent the wick when the container is disposed within the diffuser; and
- a receiver disposed in the diffuser and adjacent the wick when the container is disposed within the diffuser;
- wherein the emitter and receiver are operatively connected to detect whether the container is disposed in the diffuser; and wherein when the container is disposed within the diffuser and active material is present within the wick, light emitted by the emitter is retracted through the wick and at least some of the emitted light is received by the receiver and, when no active material. is present within the wick, light emitted by the emitter enters a dry wick and is absorbed by the wick and none of the emitted light is received by the receiver.

11. The system of 10, wherein the emitter and receiver are positioned such that when the receiver does not receive a detectable signal from the emitter, a condition that the container is empty is indicated by the system.

12. The system of claim 10. wherein the emitter and receiver are positioned such that when the receiver receives a detectable signal from the emitter. a condition that the container is absent from the diffuser is indicated by the system.

* * * * *

UNITED STATES PATENT AND TRADEMARK OFFICE
CERTIFICATE OF CORRECTION

PATENT NO. : 7,589,340 B2  Page 1 of 1
APPLICATION NO. : 11/096920
DATED : September 15, 2009
INVENTOR(S) : Dancs et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 961 days.

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,589,340 B2 | Page 1 of 1 |
| APPLICATION NO. | : 11/096920 | |
| DATED | : September 15, 2009 | |
| INVENTOR(S) | : Imre J. Dancs et al. | |

It is certified that error appears in the above-identified patent and that said Letters Patent is hereby corrected as shown below:

Column 16, Line 48: replace "1." with --1,--

Column 16, Line 50: replace "1" with --1,--

Column 16, Line 57: replace "dctecting" with --detecting--

Column 18, Line 7: replace "retracted" with --refracted--

Column 18, Line 9: replace "material." with --material--

Column 18, Line 17: replace "10." with --10,--

Column 18, Line 19: replace "emitter." with --emitter,--

Signed and Sealed this

Twenty-sixth Day of October, 2010

David J. Kappos
*Director of the United States Patent and Trademark Office*